United States Patent [19]
Lawson et al.

[11] Patent Number: 5,728,705
[45] Date of Patent: Mar. 17, 1998

[54] METHOD OF INDUCING VASORELAXATION TO TREAT PULMONARY HYPERTENSION

[75] Inventors: Charles A. Lawson, Verona; David J. Pinsky, Riverdale; Arthur Smerling, New Rochelle; David M. Stern, Great Neck, all of N.Y.

[73] Assignee: The Trustees of Columbia University in the City of New York, New York, N.Y.

[21] Appl. No.: 131,984

[22] Filed: Oct. 4, 1993

[51] Int. Cl.$^6$ .............. A61K 61/70; A61K 31/33; C07H 19/20; C07D 473/00
[52] U.S. Cl. .............. 514/261; 514/79; 514/48; 536/26.11
[58] Field of Search .............. 514/263, 48, 79, 514/261; 536/26.11

[56] References Cited

U.S. PATENT DOCUMENTS

| | | | |
|---|---|---|---|
| 4,623,666 | 11/1986 | Kennedy | 514/754 |
| 4,956,348 | 9/1990 | Gilbard | 514/47 |
| 5,175,151 | 12/1992 | Afonso et al. | 514/63 |
| 5,191,084 | 3/1993 | Bagli et al. | 546/279 |
| 5,217,997 | 6/1993 | Levere et al. | 514/565 |
| 5,250,700 | 10/1993 | Bagli et al. | 548/366.1 |
| 5,366,977 | 11/1994 | Pollard et al. | 514/263 |
| 5,370,989 | 12/1994 | Stern et al. | 435/1 |
| 5,376,666 | 12/1994 | Duncia | 514/303 |

OTHER PUBLICATIONS

A.G. Gilman, et al., "Goodman and Gilman's The Pharmacological Basis of Therapeutics" (New York: Macmillan 1980) pp. 592–607.
Rossaint, et al., *The New England Journal of Medicine* (Feb. 11, 1993) 328(6):399–405.
Archer, et al., *J. Appl. Physiol.* (1990) 68(2):735–747.
Lawson, et al., presented at American Heart Association Meeting, Atlanta, Georgia, Nov. 8–11, 1993.
Brackett et al. Biochemical Pharmacology 39(12): 1897–1904, 1990.

*Primary Examiner*—Gary L. Kunz
*Attorney, Agent, or Firm*—John P. White

[57] ABSTRACT

This invention provides a method of selectively decreasing pulmonary vascular resistance in a subject by administering endobronchially a drug chosen from among cAMP analogs, cGMP analogs, phosphodiesterase inhibitors, nitric oxide precursors, nitric oxide donors, and nitric oxide analogs.

17 Claims, 19 Drawing Sheets

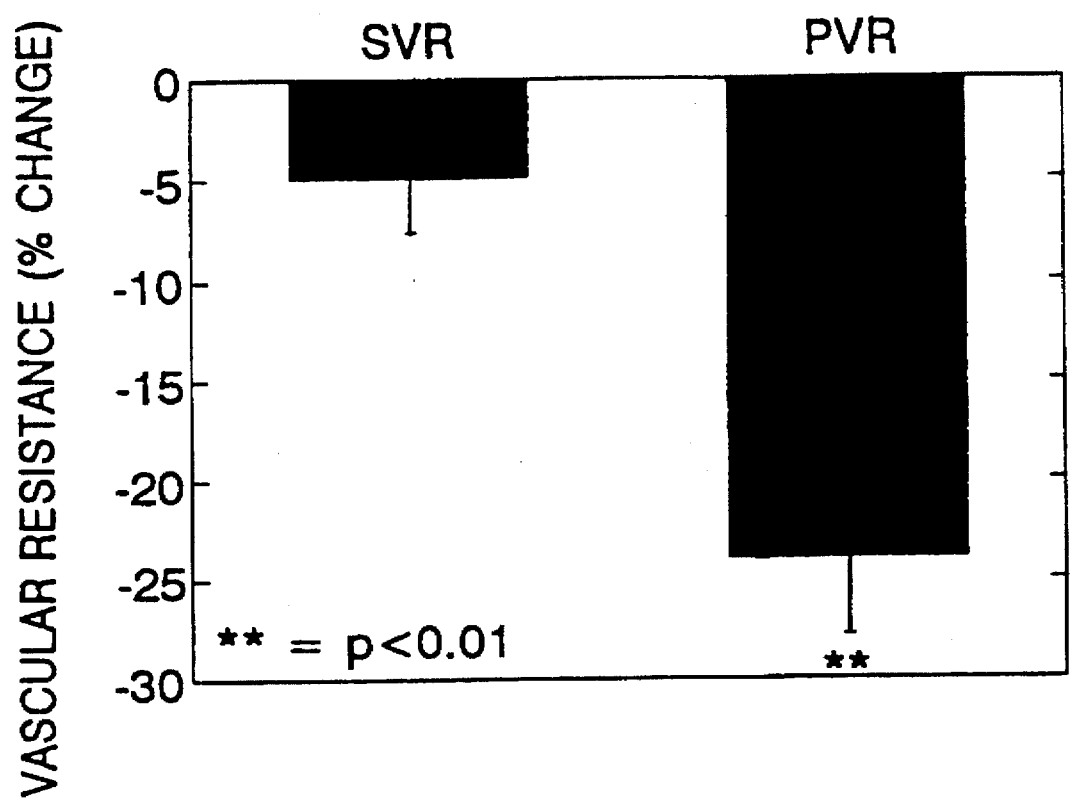

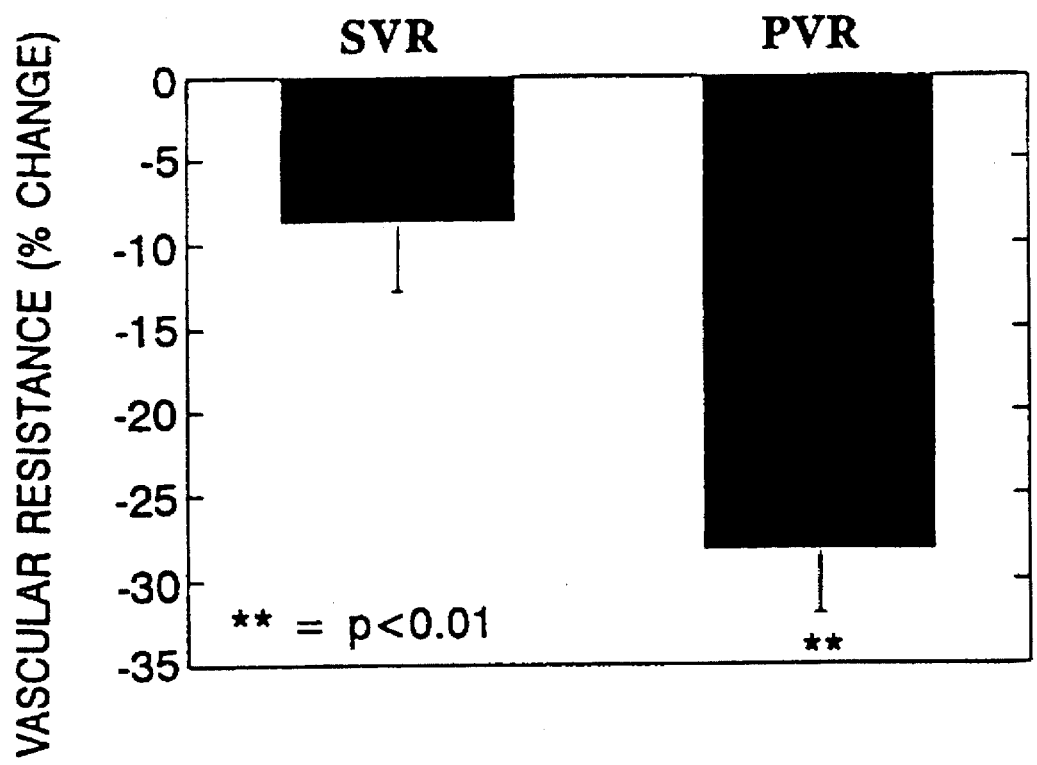

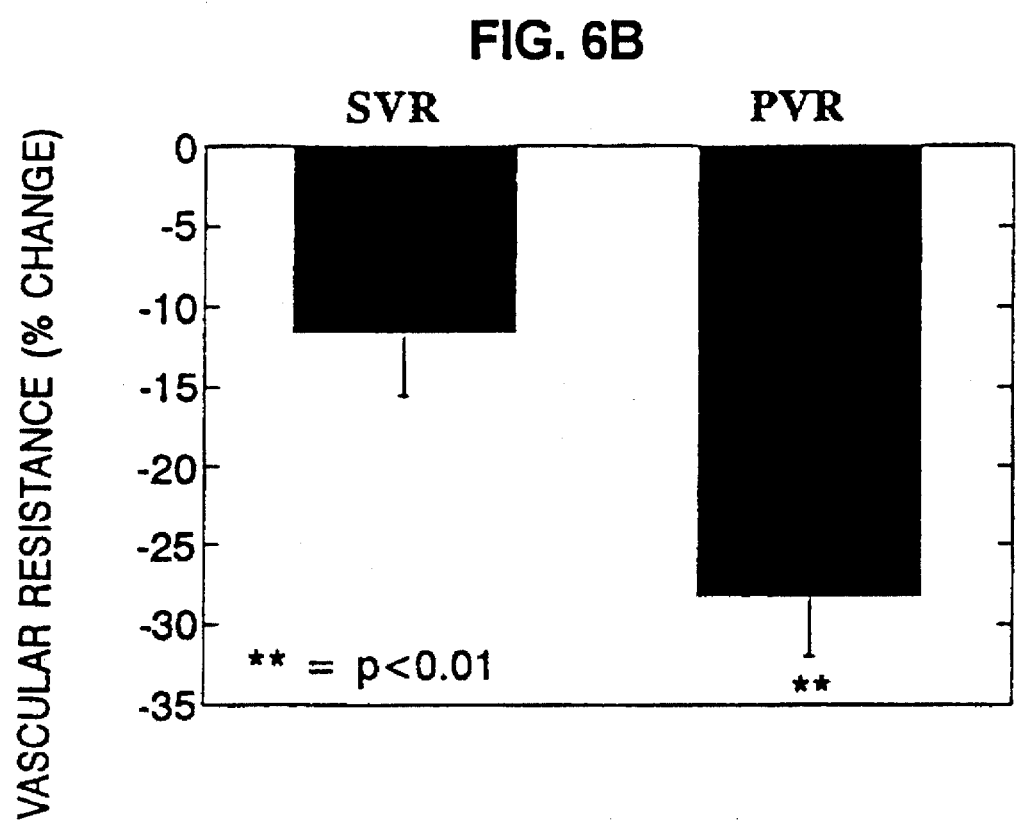

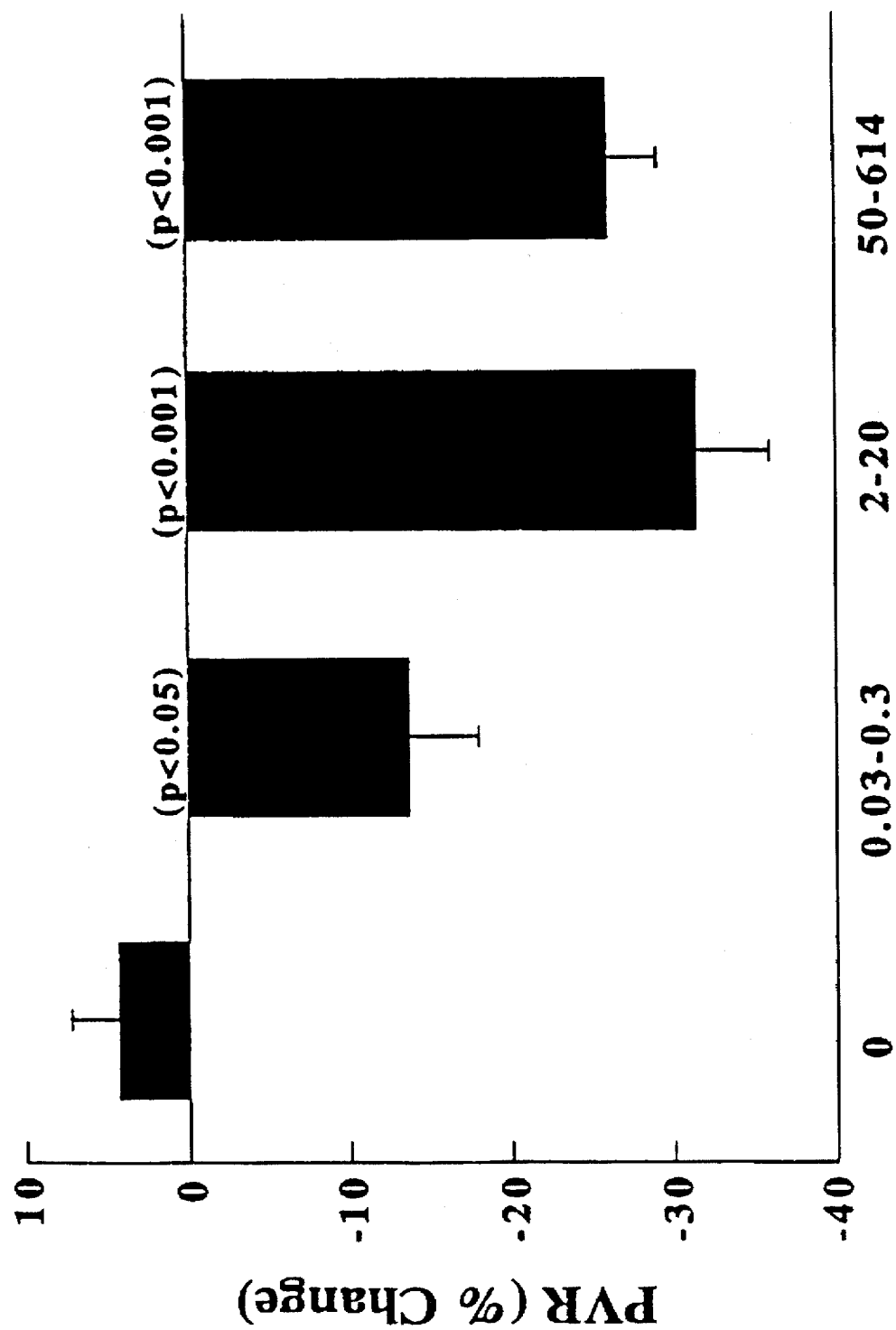

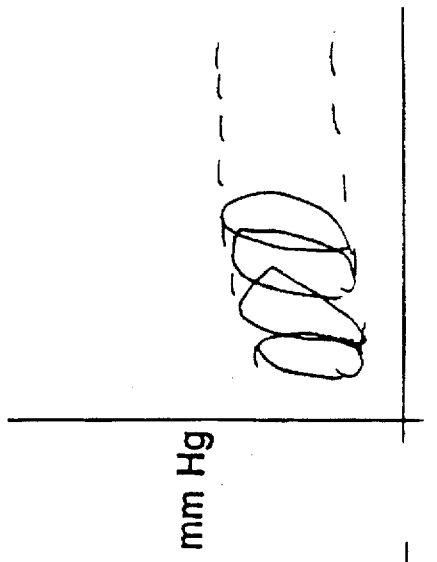
FIG. 8C  POST ESMOLOL
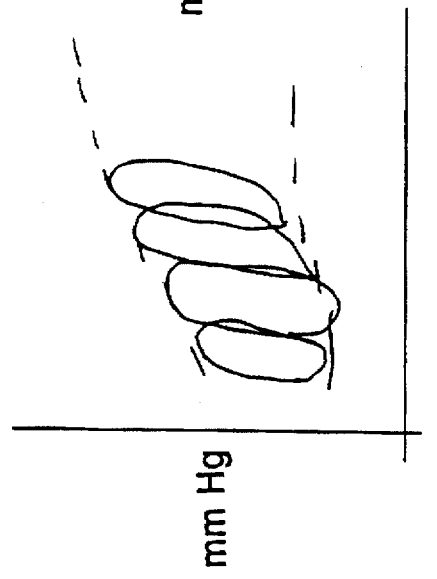
FIG. 8B  POST 8-Br-cGMP
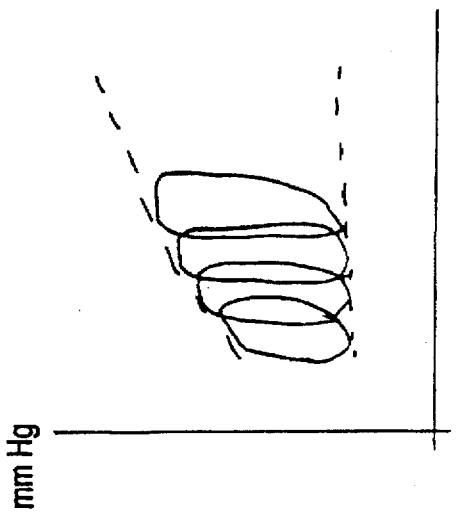
FIG. 8A  BASELINE

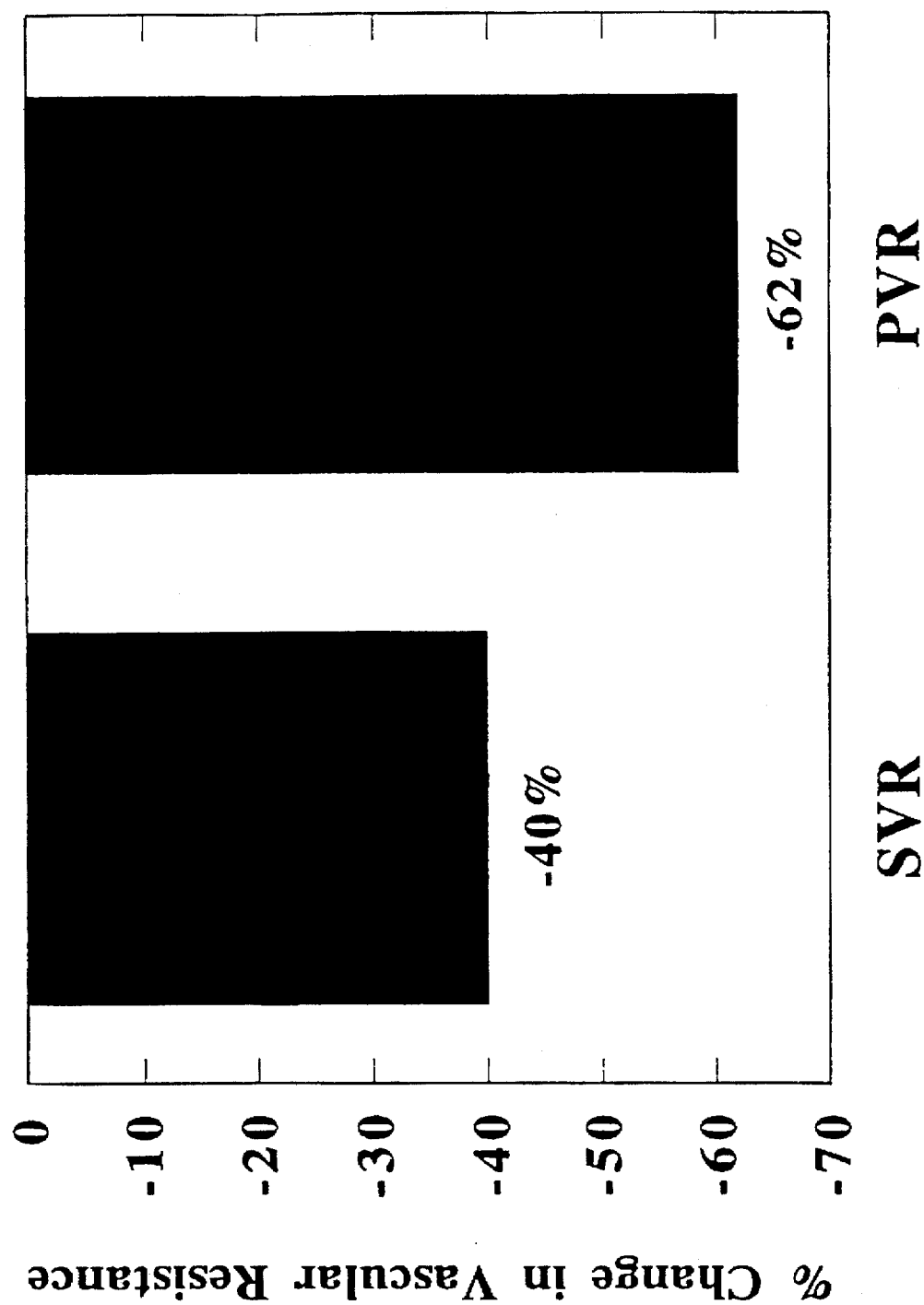

METHOD OF INDUCING VASORELAXATION TO TREAT PULMONARY HYPERTENSION

The invention disclosed herein was made with Government support under NIH Grant No. 1 T3 GMO 8464-01 from the Department of Health and Human Services. Accordingly, the U.S. Government has certain rights in this invention.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Pulmonary hypertension is associated with significant morbidity and mortality, yet therapeutic options remain limited because agents which lower pulmonary vascular resistance (PVR) also lower systemic vascular resistance (SVR) (1). Nitric oxide (NO) gas has recently been shown to selectively lower PVR in pulmonary hypertension (2,3), but concerns remain involving its potential chromosomal effects (4), formation of toxic products from reaction with oxygen (4,5), logistic difficulties associated with delivery of a gas, and its short biological half-life, necessitating constant administration for continued effect (3,6).

Initial observations dealing with the use of cAMP and cGMP compounds go back to models of heart transplantation, where it was demonstrated that these systems were dysfunctional in the blood vessels of a transplanted heart. Supplementation of either the cGMP or the cAMP pathways could enhance the function of blood vessels within the graft, promoting successful transplantation. Stimulators of cAMP pathway used in these experiments included Sp-cAMPs, 8-Br-cAMP, db-cAMP, and phosphodiesterase inhibitors (indolidan, rolipram), all of which helped graft preservation. An antagonist of this pathway (RpcAMPS) blocked the beneficial effects of 8-Br-cAMP.

Nitric oxide is formed by cells lining blood vessels from the amino acid L-arginine, and leads to the formation of cGMP in the nearby cells. In the transplantation model, compounds which give off NO (nitroglycerin, nitroprusside), the NO precursor L-arginine, or 8-Br-cGMP (which acts like native cGMP but is capable of passing through cell membranes and therefore getting into cells) similarly benefitted heart preservation.

Both pathways (cAMP and cGMP) seemed to be dysfunctional in the setting of transplantation because of their roles in maintaining proper blood vessel function. Beneficial effects included improving blood flow, reducing damaging white blood cell infiltrations into blood vessels, preventing blood vessel leakiness, and preventing blood clot formation. The basis for these effects have been described in numerous basic science papers elsewhere, in which the roles of these compounds on these functions had been studied. Experiments performed in the context of lung transplantation indicated that these same beneficial effects were found in the blood vessels of the lungs.

SUMMARY OF THE INVENTION

This invention provides a method of decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance.

This invention provides a method of selectively decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance.

DESCRIPTION OF THE FIGURES

FIGS. 3A-3B : Effect of inhaled 8-Br-cGMP on systemic (SVR) and pulmonary (PVR) vascular resistance in the thromboxane analog model of pulmonary hypertension. 8Br-cGMP was administered endotracheally as a mist (2–614 µg/kg) delivered in a 5 ml volume of physiologic saline, and hemodynamics were measured as described. (A) The maximal decline in PVR and the simultaneous decrease in SVR are expressed as mean % change [100×(MAP OR MPAP post-8-Br-cGMP minus MAP or MPAP pre-8-Br-cGMP) /MAP or MPAP pre-8-Br-cGMP]±SEM. (b) The maximal decrease in SVR is consistently less than the maximal decrease in PVR after inhalation of 8Br-cGMP. Values are as described in (A).

FIGS. 6A-6B: Effect of inhaled 8-Br-cGMP on pulmonary and systemic vascular resistance in the hypoxia-induced pulmonary hypertension. After baseline stabilization, pigs were ventilated with a hypoxic gas mixture as described in FIG. 1. (A) The maximal decline in PVR and the corresponding drop in SVR are expressed as in FIG. 2. (B) Maximal decline in PVR was compared with maximal decline in SVR as described for the thromboxane analog model in FIG. 2.

FIGS. 7A–7B: Effect of 8-Br-cGMP on pulmonary hypertension: time course and dose-response. (A) Time course of effect of 8-Br-cGMP on PVR in the thromboxane analog and hypoxia models of pulmonary hypertension. Peak effect of 8-Br-cGMP to lower PVR is observed approximately 70 minutes following inhalation. Times shown represent measurements taken at the indicated times±10 minutes. (B) Dose-response of inhaled 8-Br-cGMP on PVR demonstrates maximal reduction in PVR at doses between 2–20 µg/kg. ($p<0.001$ vs physiologic saline. control).

FIGS. 8A–8C: Effect of inhaled 8-Br-cGMP on load-independent measurement of ventricular function. Pressure volume loops were recorded with a conductance catheter placed in the left ventricle under fluoroscopic guidance, with intermittent caval occlusion performed to vary preload. Hypertonic saline was administered to standardize the conductance measurements (15), and esmolol (40 mg as an intravenous bolus) was given to demonstrate the effects of a known negative inotrope (data not shown). Systolic and diastolic function are described by the upper and lower tangents (respectively) to the pressure volume curve families, and are not different when compared before (A) or after (B) inhalation of 8-Br-cGMP (30 µg/kg) in 5 ml of normal saline delivered as a mist. Measurements were recorded for two hours (the 60 minute data is shown; there was no difference in ventricular function noted at any time point).

FIG. 9: Percent change in SVR and PVR upon administration of Sp-8-Br-cGMPS (Thromboxane model).

DETAILED OF THE INVENTION

Figure 1A:
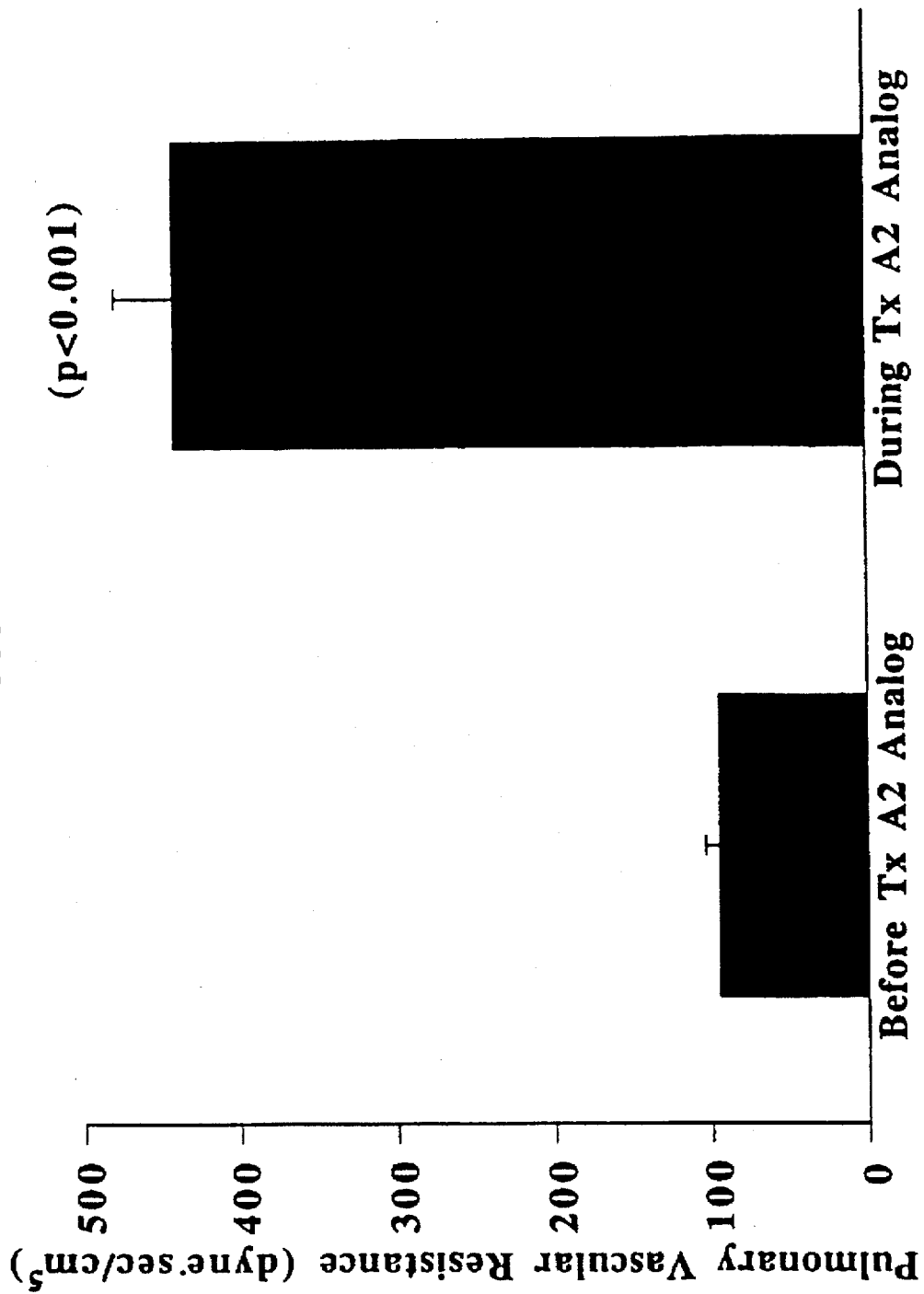
FIGS. 1A-1C : Establishment of pulmonary hypertension in three porcine models. (A) The thromboxane (Tx) $A_2$ analog 9,11-dideoxy-11α, 9α-epoxymethanoprostaglandin $F_{2\alpha}$ was infused intravenously (n=9) initially at 0.1 µg/kg/min, and titered until a stable mean PA pressure of 30 mmHg was reached, after which no dosage adjustments were made. Bar graphs represent the mean ±SEM of the baseline measurements of pulmonary vascular resistance (PVR) versus those obtained 1 hour after a stable dose of Tx was achieved (range 0.07–0.11 µg/kg/min). (B) Hypoxic pulmonary artery vasoconstriction was induced (n=8) by ventilation with a gas mixture consisting of nitrogen and oxygen mixed so that inhaled $O_2$ was 9–10%. Bar graphs represent the mean±SEM of the baseline measurements of PVR versus those obtained after hypoxic ventilation. (C) ARDS model of pulmonary hypertension was created by infusing oleic acid (0.3 ml/kg, n=6) over 1–2 hours, followed by measuring PVR±SEM after stable measurements were recorded during a one hour period.

This invention provides a method of decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. Administering endotracheally means administering via the trachea. Administering endobronchially means administering via a bronchus or bronchi. As used herein bronchus refers to one of the primary divisions of the trachea or to one of the further divisions which connect the primary bronchi and the bronchioles.

In a specific embodiment of this method, pulmonary vascular resistance is decreased by at least about twenty-four percent. In another embodiment, the pulmonary vascular resistance is decreased by up to about thirty-four percent. In a preferred embodiment, PVR is decreased by up to about sixty-four percent. In another embodiment, the pulmonary vascular resistance is decreased between about twenty-four percent and about thirty-four percent. In another embodiment, the pulmonary vascular resistance is decreased between about twenty-four percent and about sixty-four percent.

In a preferred embodiment, the pulmonary vascular resistance is decreased for over ninety minutes. In a specific embodiment maximal decrease in pulmonary vascular resistance occurs at about seventy minutes after administering the drug.

This invention also provides for a method of selectively decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. Selectively decreasing pulmonary vascular resistance means decreasing pulmonary vascular resistance by a greater degree than systemic vascular resistance is decreased. In a specific embodiment, the ratio of the percent change in systemic vascular resistance to the percent change in the pulmonary vascular resistance ($\Delta SVR/\Delta PVR$) is about 0.5 or less. In a more specific embodiment, the ratio of the percent change in systemic vascular resistance to the percent change in the pulmonary vascular resistance ($\Delta SVR/\Delta PVR$) is about 0.3 or less. In a preferred embodiment, the ratio of the percent change in systemic vascular resistance to the percent change in the pulmonary vascular resistance ($\Delta SVR/\Delta PVR$) is about 0.04 or less.

This invention also provides for a method of selectively counteracting the effects of a vasoconstrictor which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. The vasoconstrictor may be a product of the subject's own body or it may be a vasoconstrictor that is administered to the subject. The drug may be administered before, during, or after the vasoconstrictor is administered. In a specific embodiment, the vasoconstrictor is thromboxane $A_2$. In another specific embodiment the vasoconstrictor is thromboxane $A_2$ analog U-46619.

This invention provides for a method of treating pulmonary hypertension in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance.

This invention also provides for a method of treating a pulmonary condition in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. In an embodiment of this method the pulmonary condition is selected from the group consisting of primary pulmonary hypertension, chronic obstructive pulmonary disease, adult respiratory distress syndrome, congenital heart disease, asthma, cystic fibrosis, sarcoidosis, cor pulmonale, pulmonary embolism, bronchiectasis, emphysema, Pickwickian syndrome, sleep apnea, congestive heart failure, and valvular heart disease.

In the method of decreasing pulmonary vascular resistance in a subject, the subject may be any animal with lungs or lung-like structures. In a specific embodiment, the subject is a mammal. In a more specific embodiment, the mammal is a pig. In another specific embodiment, the mammal is a human.

In an embodiment, the administering comprises injecting a liquid containing the drug via the trachea or a bronchus.

In another embodiment the administering comprises inhaling the drug in an aerosol form. In a specific embodiment the aerosol particle size is between about 0.5 micrometers and about 10 micrometers.

In a specific embodiment the aerosol is generated by a nebulizer.

In one embodiment the aerosolized drug is administered as an aqueous solution. Preferably, the aerosolized drug is administered as a lipid soluble aqueous solution. In another embodiment the aerosolized drug is administered as a micronized powder.

This invention also provides a method of decreasing pulmonary vascular resistance in a subject which comprises administering endotracheally or endobronchially an effective amount of a cyclic nucleotide, thereby decreasing pulmonary vascular resistance.

In an embodiment the cyclic nucleotide is membrane permeant. In another embodiment the cyclic nucleotide is an agonist of protein kinase A. In another embodiment the cyclic nucleotide is an agonist of protein kinase G. In another embodiment the cyclic nucleotide increases cellular cAMP. In another embodiment the cyclic nucleotide increases cellular cGMP. In another embodiment the cyclic nucleotide is resistant to degradation by an enzyme. In a specific embodiment, the cyclic nucleotide is resistant to degradation by phosphodiesterase.

In an embodiment the cyclic nucleotide is a cGMP analog. In a specific embodiment the cGMP analog is 8-bromo-3', 5'-cyclic guanosine monophosphate. In another embodiment the cGMP analog is 8-PCPT-cGMP. In another embodiment the cGMP analogue is Sp-8-Br-cGMPS.

In an embodiment the cyclic nucleotide is a cAMP analog. In a specific embodiment the cAMP analog is dibutyryl-3', 5'-cyclic adenosine monophosphate. In another embodiment the cAMP analog is 8-bromo-3', 5' cyclic adenosine monophosphate. In another embodiment the cAMP analog is Sp-cAMPS.

In an embodiment the effective amount of the drug is at least about 0.03 micrograms per kilogram of body weight. In a more specific embodiment the effective amount of the drug is between about 2 micrograms per kilogram of body weight to about 20 micrograms per kilogram of body weight.

In an embodiment the effective amount of 8-bromo-3', 5' cyclic guanosine monophosphate is at least about 0.03 micrograms per kilogram of body weight. In a preferred embodiment the effective amount of 8-bromo-3', 5' -cyclic guanosine monophosphate is between about 2 micrograms per kilogram of body weight to about 20 micrograms per kilogram of body weight.

This invention also provides for the method of decreasing pulmonary vascular resistance further comprising administering a permeabilizing solvent. A permeabilizing solvent is a solvent which facilitates the passage of the drug through the cell membrane of the cells of the trachea or bronchus, particularly when the drug is a cyclic nucleotide. In a preferred embodiment the permeabilizing solvent is dimethylsulfoxide.

This invention also provides a method of decreasing pulmonary vascular resistance in a subject which comprises administering endotracheally or endobronchially an effective amount of a phosphodiesterase inhibitor, thereby decreasing pulmonary vascular resistance. In a specific embodiment the phosphodiesterase inhibitor is selected from the group consisting of isobutylmethylxanthine, indolidan, 1,3dihydro-3,3dimethyl-5-(1,4,5,6-tetrahydro-6-oxo-3-pyridazinyl) -2H-indol-2one rolipram, 4-[3 (cyclopentyloxy) -4-methoxyphenyl]-2-pyrrolidinone 2-o-propoxyphenyl-8-azapurin-6-one (M&B 22948; Zaprinast), trequensin 2,3,6,7-tetrahydro-9,10-dimethoxy-3-methyl-2-[ (2,4,6-trimethylphenyl) imino]4H-pyrimido [6,1, -$\alpha$]isoquinolin-4-one, amrinone 5-amino-[3,4'-bipyridin]-6 (1H) one and milrinone 1,6-dihydro-2methyl-6-oxo-(3,4'-bipyridine) -5-carbonitrile. In a more specific embodiment the phosphodiesterase inhibitor is isobutylmethylxanthine. In another specific embodiment the phosphodiesterase inhibitor is 2-o-propoxyphenyl-8-azapurin-6-one (M&B 22948).

This invention also provides a method of decreasing pulmonary vascular resistance in a subject which comprises administering endotracheally or endobronchially an effective amount of drug selected from the group consisting of nitric oxide precursors, nitric oxide donors, and nitric oxide analogs, thereby decreasing pulmonary vascular resistance.

In a specific embodiment, the nitric oxide precursor is L-arginine. In a specific embodiment the nitric oxide donor is selected from the group consisting of diethylamine NONOate and spermine NONOate. In an embodiment, the nitric oxide analog is selected from the group consisting of nitroglycerin, nitroprusside, Sin-1, and SNAP. In an embodiment, the nitric oxide donor is selected from the group consisting of nitroglycerin, nitroprusside, Sin-1, and SNAP.

This invention will be better understood from the Experimental Details which follow. However, one skilled in the art will readily appreciate that the specific methods and results discussed are merely illustrative of the invention as described more fully in the claims which follow thereafter.

Experimental Details

There are currently no effective therapies for pulmonary hypertension. Although the gas nitric oxide (NO) selectively dilates the pulmonary vascular bed, it is difficult to administer, has a short biologic half-life, and is potentially toxic. It was hypothesized that stimulation of the nitric oxide pathway using a nonhydrolyzable, membrane permeant analog of cGMP such as 8-Br-cGMP (7,8,9) or Sp-8-Br-cGMPS, or the cAMP analogs dibutyryl cAMP or 8-Br-cAMP which are administered via inhalation would confer relative pulmonary selectivity and circumvent the difficulties associated with administration of NO. These studies using three porcine models of pulmonary hypertension demonstrate the potential therapeutic usefulness of administering cGMP/cAMP analogs for the treatment of pulmonary vasoconstrictive disorders. Pulmonary hypertension was induced in 23 pigs by an intravenous thromboxane $A_2$ analog, U-46619, (Tx, n=9), hypoxic ventilation (H, n=8), or oleic acid (OA, n=6). Because NO increases cyclic guanosine 3'-5'-monophosphate (cGMP) levels in vascular smooth muscle, tests were done to determine whether inhalation of a membrane permeable cGMP analog to cause the highest possible pulmonary concentrations could cause selective pulmonary vasodilation in several models of pulmonary hypertension. In a comparison of aerosolized intratracheal inhalation of 8Br-cGMP with physiologic saline, pulmonary vascular resistance (PVR) declined by 24±3.8% (p<0.001), 28±3.7% (p<0.01), and 34±8.1% (p<0.05), for the Tx, H, and OA models, respectively. This compares favorably with PVR reduction seen following inhaled NO (50 ppm) (ΔPVR for 8-Br-cGMP was 50% of the ΔPVR for NO in the Tx model). The declines in systemic vascular resistance (SVR) following intratracheal 8Br-cGMP (1±4% and 9±4%, respectively was significantly less (P<0.01) than the declines in PVR in the Tx and H models, but were similar in the OA model. Intravenous 8Br cGMP lowers PVR and SVR to a similar degree. 8Br-cGMP lowers PVR in a time and dose-dependent manner, with maximal effect achieved after one hour at doses as low as 0.03 μg/kg. The selective decline in PVR was not mimicked by inhalation of guanosine-5'monophosphate, suggesting that stimulation of the NO/cGMP pathway beyond the level of NO results in selective pulmonary vasodilation independent of stimulation of purine receptors. Pressure-volume loops constructed at different preloads using an intraventricular conductance catheter demonstrate little effect of inhaled 8Br-cGMP on ventricular contractility, suggesting that this agent may be given safely in the setting of cor pulmonale. These studies demonstrate that inhalation of an agent which is an analog of cGMP can selectively reduce PVR, and may be useful in pulmonary vasoconstrictive diseases.

EXPERIMENTAL METHODS

This experimental protocol was approved by the Columbia University Institutional Animal Care and Use Committee. Female swine (Hampshire or Yorkshire breeds, 35–70 kg) were premedicated, intubated, anesthetized and given a continuous infusion of muscle relaxant. The electrocardiogram was monitored (Datascope 2000, Datascope, Paramus, N.J.). Ventilation was controlled with an Ohmeda 7000 anesthesia ventilator (Ohmeda, Madison, Wis.) attached to an Ohmeda VMC anesthesia machine (BOC, W. Yorkshire, UK). Respiratory gases and airway pressures were monitored with an Ohmeda RGM 5250 analyzer (Ohmeda, Louisville, Colo.). An arterial catheter was inserted percutaneously into the femoral artery and the right external jugular vein was exposed via cutdown. An 8.5 F introducer sheath (Arrow, Reading, Pa.) was inserted into the external jugular vein, followed by placement of a 7.5 F pulmonary artery thermodilution catheter (Baxter Edwards Critical Care, Irvine, Calif.) which was advanced to the pulmonary artery with hemodynamic monitoring. Arterial, pulmonary artery, central venous, and pulmonary capillary sedge pressures were transduced (Abbott, North Chicago, Ill.) at right atrial level, and displayed on Datascope 2000 monitors (Paramus, N.J.). Animal temperature was measured continuously by rectal probe and maintained by infrared heating lamps. A cardiac output computer (Edwards Critical Care, Irvine, Calif.) using the thermodilution technique was used to measure cardiac output. Blood gas measurements for pH, $CO_2$ and $O_2$ content (mm Hg), and hemoglobin oxygen saturation were performed on a calibrated arterial blood gas analyzer (Nova Biomedical, Waltham, Mass.).

Hemodynamics were recorded at end expiration at baseline and every 10–15 minutes thereafter, and included measurements of heart rate (HR, beats/min), central venous pressure (CVP, mm Hg), pulmonary artery wedge pressure (PCWP, mm Hg), mean arterial and mean pulmonary arterial pressures (MAP, MPAP, mm Hg), and thermodilution cardiac outputs (CO, L/min). Three repetitive measurements of cardiac output using iced saline injection were averaged for each time point. When a stable baseline PVR was demonstrated, pulmonary hypertension was induced by 1) continuous intravenous infusion of the thromboxane $A_2$ analog (9,11-dideoxy-11α, 9α-epoxymethanoprostaglandin $F_{2\alpha}$ (10) (Sigma Chemical Co., St. Louis, Mo.) at a rate which resulted in a mean PA pressure of ≈30 mm Hg (0.07–0.11 μg/kg/min); 2) ventilation with a hypoxic gas mixture containing oxygen and nitrogen with the proportion of oxygen titrated to a mean PA pressure ≈30 mm Hg, with continuous hypoxia monitored by inhaled (≈10%) and arterial ($paO_2$) ≈35 mm Hg) oxygenation; 3) intravenous infusion of oleic acid (Sigma) 0.3 ml/kg over 1 hour. After stable measurements of PVR in the hypertensive state were achieved, aerosolized physiologic saline (0.9% sodium chloride) was given endotracheally, followed by at least one hour of observation. After observing consistent measurements of PVR, 8Br-cGMP (Sigma) was then given endotracheally (0.03–614 μg/kg in a 5 ml volume of physiologic saline, administered over 5 minutes) and hemodynamic data were recorded every 10–15 minutes. The normal saline and test compounds dissolved in normal saline were delivered endotracheally as a mist. Intravenous administration consisted of dissolving 300 μg/kg 8Br-cGMP in 5 ml of physiologic saline and injecting the solution as a bolus. In other experiments, 8-bromoguanosine-5'monophosphate (272 μg/kg, Sigma), Sp-cGMPS (Biolog, La Jolla, Calif.), dibutyryl cAMP (db-cAMP) or 8-Br-cAMP were similarly administered. NO (Airco, Lodi, N.J.) at a concentration of 50 ppm was administered during controlled ventilation after repeated measurements indicated unchanging pulmonary hypertension. At least 10 minutes of continuous NO inhalation elapsed before hemodynamic measurements were taken.

Measurement of Ventricular Function: Previous reports have suggested that NO and 8-Br-cGMP may exert some direct negative inotropic actions (11–14). In order to assess whether 8Br-cGMP has any such effects, experiments were performed in 2 animals in which pulmonary hypertension was not induced. LV contractile state was assessed in these animals by measuring the end-systolic pressure-volume relations (ESPVR). A 7 F conductance catheter (10 pole, Webster Labs Inc., Baldwin Park, Calif.) was introduced into the carotid artery and the tip positioned in the left ventricular apex under fluoroscopic guidance. The abdominal inferior vena cava was exposed and venous return was impeded as needed with a snare. Conductance measurements were calibrated by estimating parallel conductance with a 10 ml bolus of hypertonic saline (5%) as described previously (15,16). LV pressure was measured using a Statham strain gauge connected to the end lumen in the conductance catheter. Data were digitized 200 Hz sampling rate) on a PC compatible computer and analyzed off-line with custom designed software. Pressure-volume loops were obtained at different preloads during brief periods of IVC occlusion, and end-systolic pressure ($P_{es}$) and volumes ($V_{es}$) were identified in the standard fashion. The slope ($E_{es}$) and volume axis intercept ($V_o$) were calculated using linear regression analysis of $V_{es}$ against $P_{es}$: $P_{es}=E_{es}(V_{es}-V_o)$. 8Br-cGMP was administered as described above and ESPVR measurements were taken every 15 minutes for 2 hours. To gauge the effect of a known negative inotrope, an intravenous bolus of esmolol (1 mg/kg) was given after the 2 hour period, and the same measurements were obtained. The other cyclic nucleotides were administered similarly.

Calculations and Statistics: CVP, PCWP, MAP, MPAP, and CO were recorded. Pulmonary vascular resistance (PVR, dynes.sec/$cm^5$) and systemic vascular resistance (SVR, dynes.sec/$cm^5$) were calculated as follows; PVR=80-(MPAP−PCWP)/CO; SVR=80.(MAP−CVP)/CO. For each animal, the PVR and SVR were calculated under the baseline conditions, and when consistent serial measurements were obtained, pulmonary hypertension was induced using one of the methods. PVR and SVR in the hypertensive state prior to administration of the test compound were compared to the lowest PVR and SVR values recorded after administration of the test compound. Each animal contributed a single data point to the statistical calculations. Pre- and post-treatment values were compared using the paired Student t-test to discriminate significant differences. Data was considered statistically significant if p<0.05. The effect of 8Br-cGMP on arterial oxygenation was recorded simultaneously with the greatest drop in PVR. Time course data were analyzed using ANOVA, using Tukey's test to discriminate significant differences between group means. Data was considered significant if p<0.05.

EXPERIMENTAL RESULTS

8-Br-cGMP

Figure 1B:
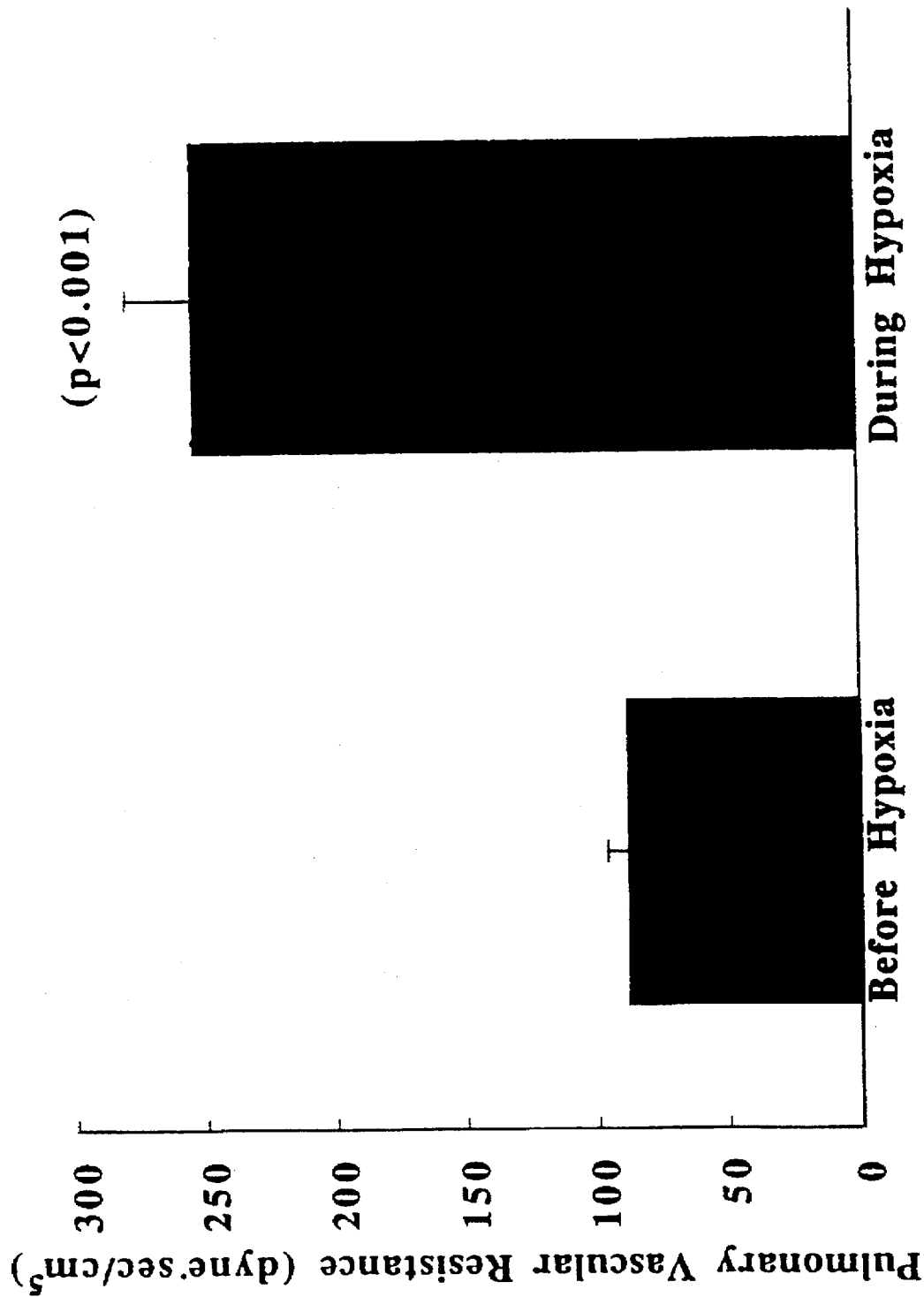
Figure 1C:
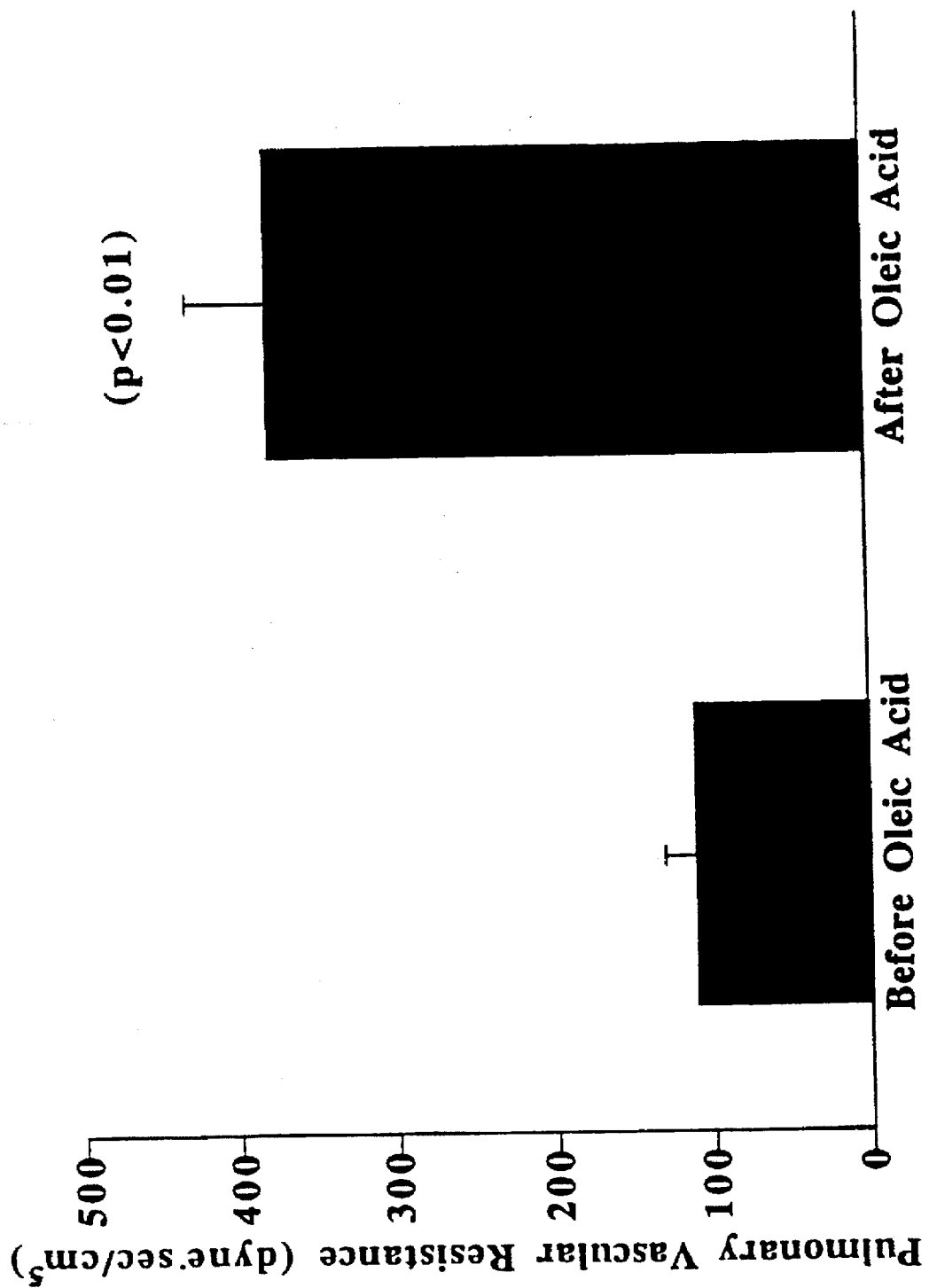
Figure 2A:
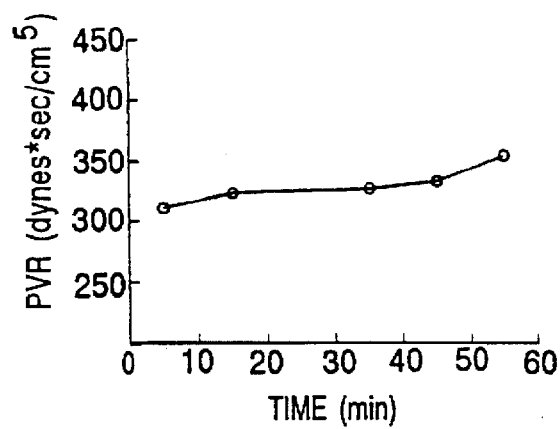
FIGS. 2A-2J : Simultaneous hemodynamic measurements from a representative animal following the establishment of pulmonary hypertension in the thromboxane analog model. (A-E) Physiologic saline inhalation (5 ml). (F-J) 8Br-cGMP inhalation (5 ml in physiologic saline, 3.3 µg/kg). Measurements include heart rate (HR, beats/min), central venous pressure (CVP, mm Hg), pulmonary artery wedge pressure (PCWP, mm Hg), mean arterial and mean pulmonary arterial pressures (MAP, MPAP, mm Hg), and thermodilution cardiac outputs (CO, L/min).
Figure 2B:
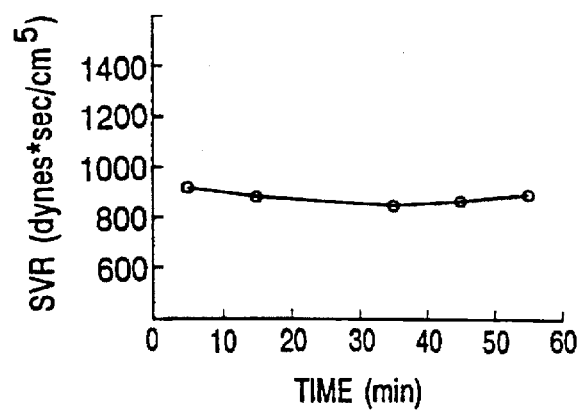
Figure 2C:
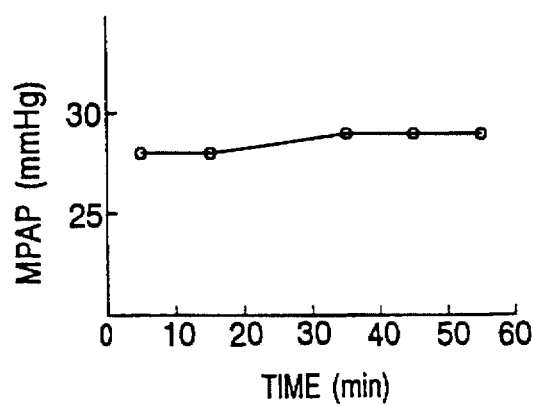
Figure 2D:
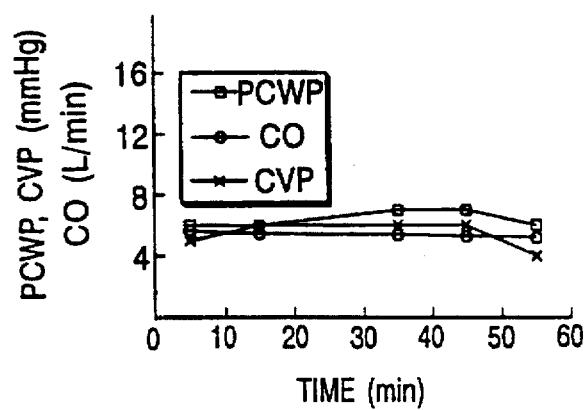
Figure 2E:
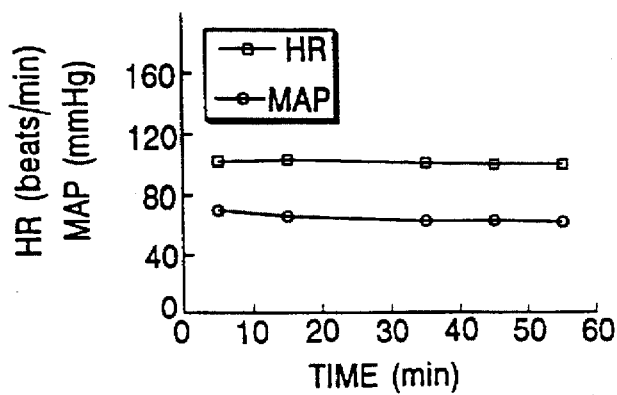
Figure 2F:
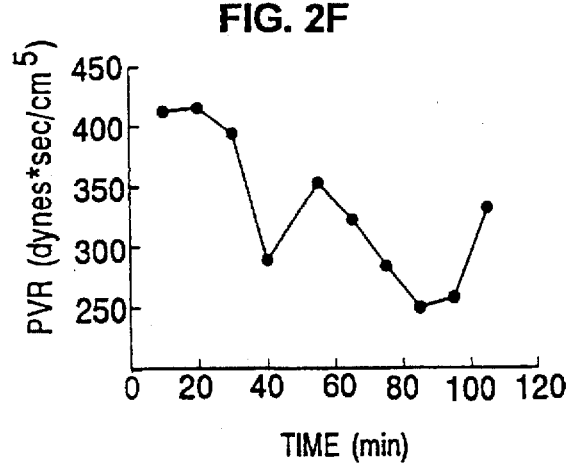
Figure 2G:
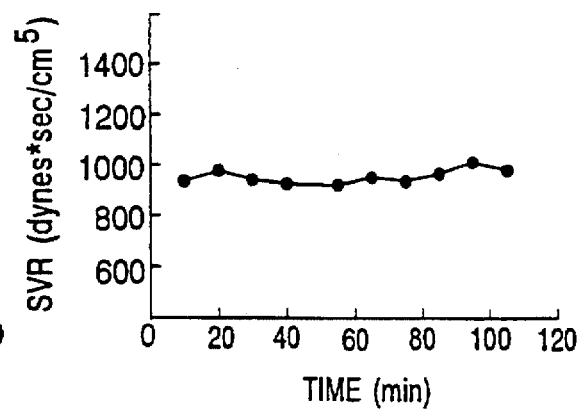
Figure 2H:
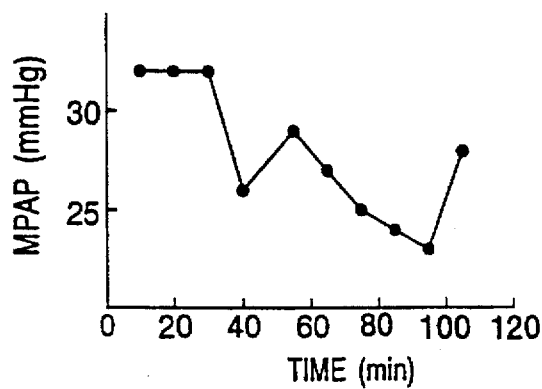
Figure 2I:
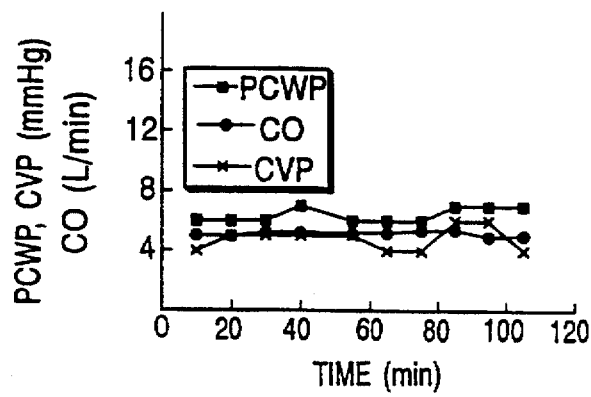
Figure 2J:
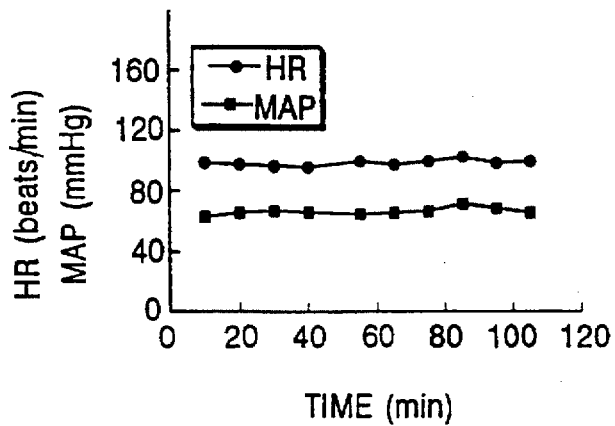

Three porcine models of pulmonary hypertension were established: a vasoconstrictor model using an intravenous infusion of the thromboxane $A_2$ analog (n=9), a model of hypoxia-induced pulmonary vasoconstriction (n=8), and a model of ARDS created by intravenous injection of oleic acid (n=6). In each of these models, baseline hemodynamic measurements were initially recorded and then pulmonary hypertension was induced as described (FIGS. 1A–1C). In the thromboxane model, PVR increased by 364±8.8% (p<0.001 vs. baseline). In the hypoxia model PVR increased by 187 ±8.4% vs. baseline (p<0.001). The ARDS model demonstrated an increase in PVR following oleic acid administration by 241±17% (p<0.01).

Figure 3A:
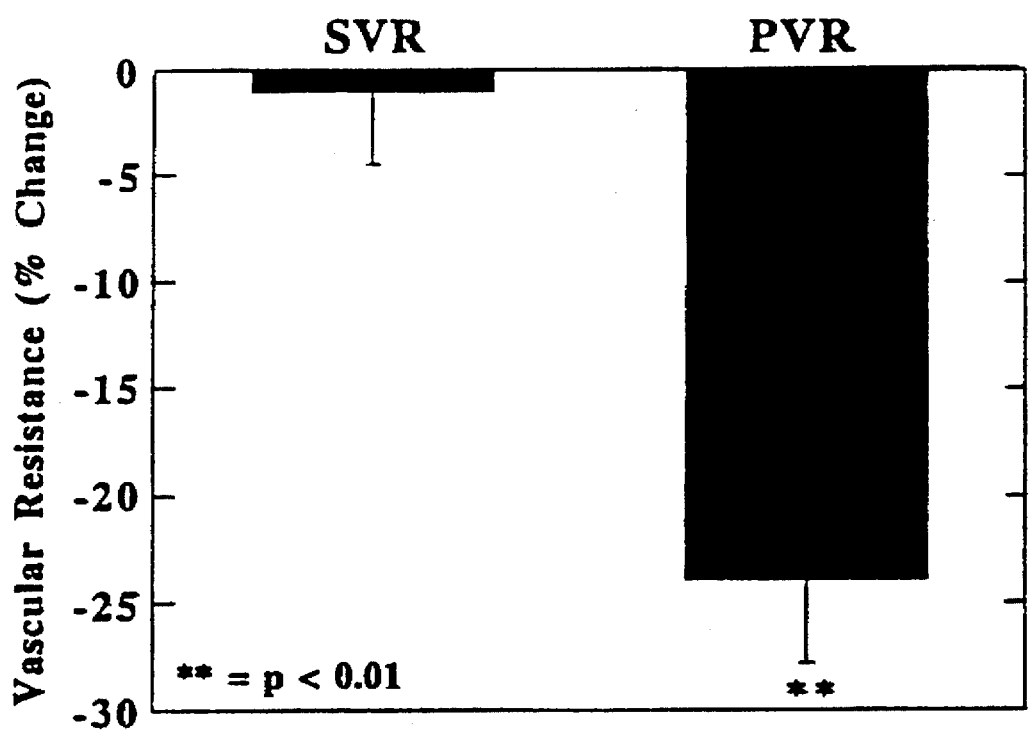
Figure 4A:
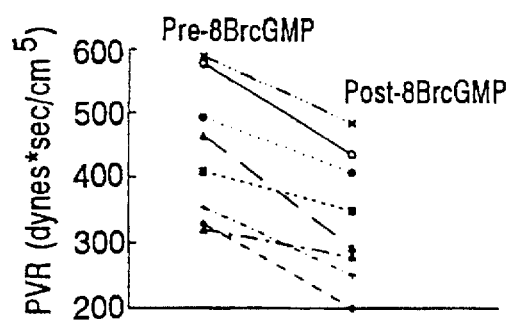
FIGS. 4A-4H: Hemodynamic data in the thromboxane analog model of pulmonary hypertension before and after inhalation of 8Br-cGMP. Each symbol represents a single animal.
Figure 4B:
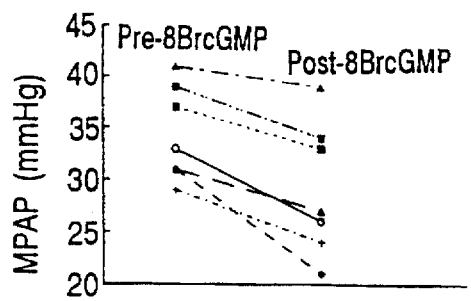
Figure 4C:
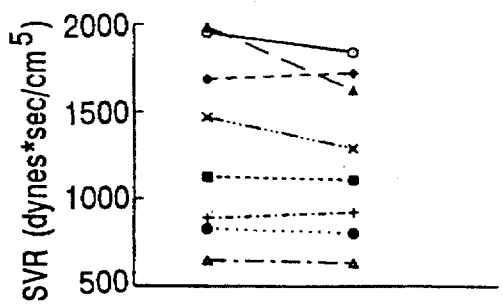
Figure 4D:
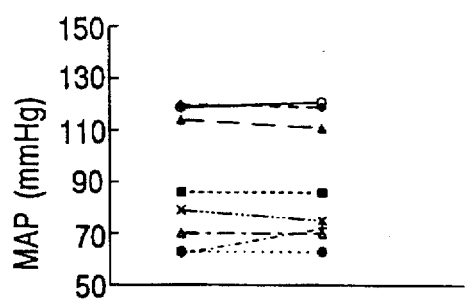
Figure 4E:
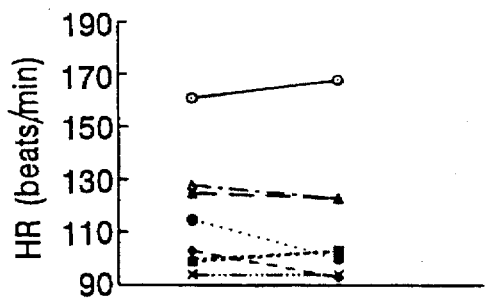
Figure 4F:
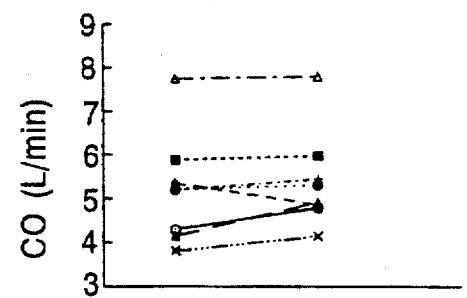
Figure 4G:
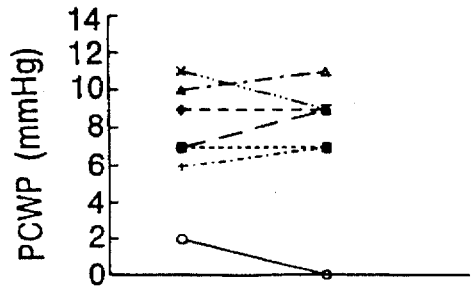
Figure 4H:
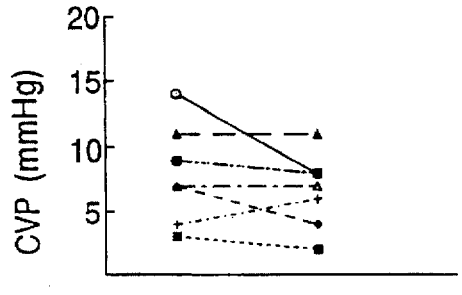

The effects of an inhaled membrane-permeable analog of cGMP, 8Br-cGMP, on PVR and SVR were studied in each of the three models of pulmonary hypertension to determine whether this compound and method of administration might confer relative selectivity for the pulmonary vasculature. Hemodynamic measurements of a representative animal in the thromboxane model are shown after physiologic saline inhalation (FIGS. 2A–2E) and 8Br-cGMP inhalation (FIGS. 2F–2J). In the thromboxane model, the decrease in PVR after inhalation of 8Br-cGMP was significant when compared with inhalation of the physiologic saline vehicle (−23.9±3.8% vs. 7.6±3.5%, p<0.001). PVR dropped significantly more than did the corresponding SVR (23.9% vs. 1.1%, respectively p<0.01) following inhalation of 8Br-cGMP (FIG. 3A). To establish that this selective response was not simply due to delayed distribution of the compound to the systemic vasculature, the maximal declines in PVR and SVR were recorded following administration (FIG. 3B). This comparison demonstrated that even when the maximal decline in SVR was recorded, inhaled 8-Br-cGMP remains a relatively selective pulmonary vasodilator.

The drop in PVR in the thromboxane analog model following inhaled 8Br-cGMP was predominantly due to its effects to decrease mean pulmonary arterial pressure although there was an improvement in cardiac output in some animals. Other hemodynamic variables (including PCWP, HR, MAP, CVP, and SVR) remained relatively stable (FIGS. 4A–4H).

Figure 5:
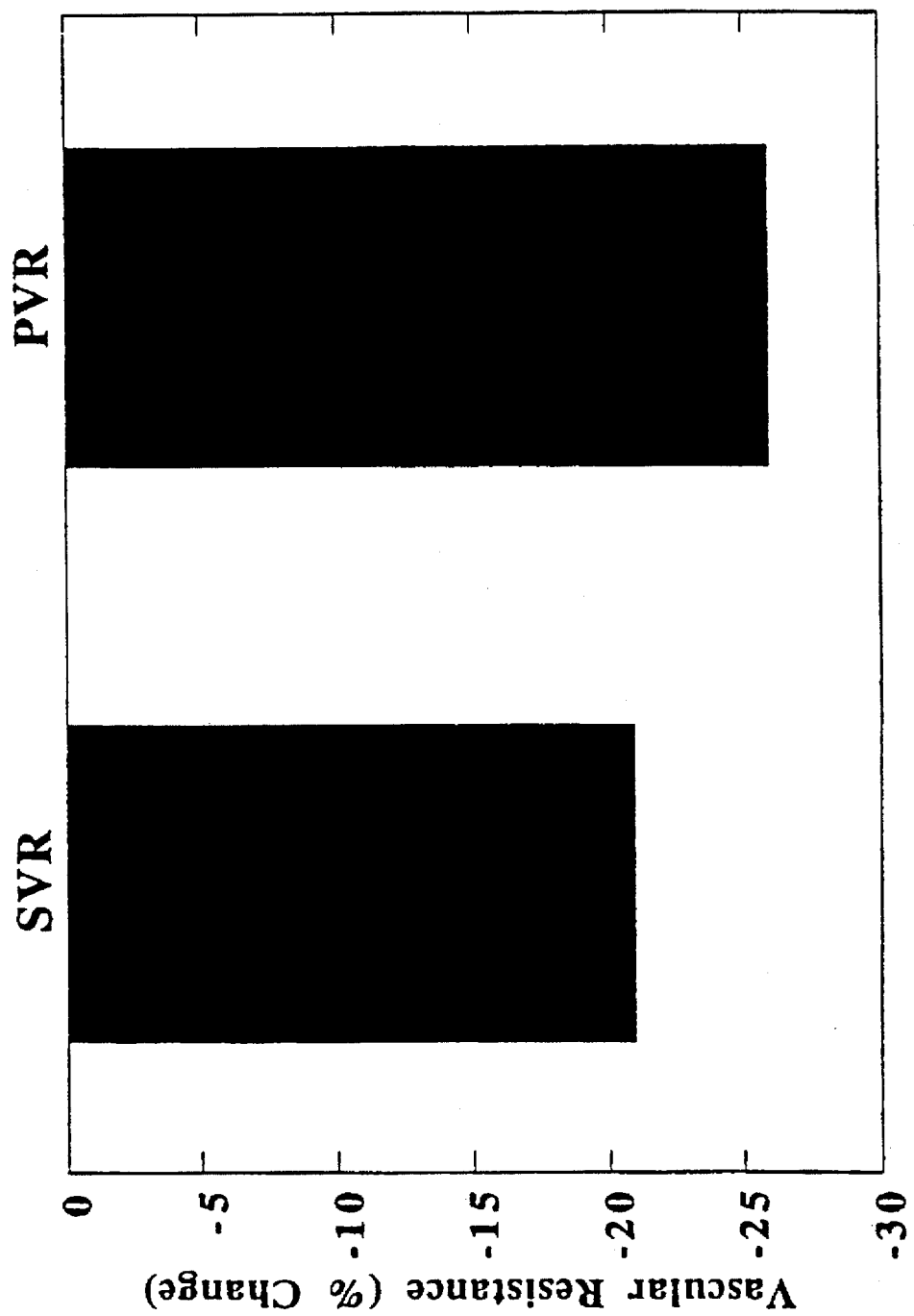
FIG. 5: The maximal % decreases in SVR and PVR after intravenous administration of 8Br-cGMP (300 µg/kg) in the thromboxane analog model.

To assess the relative selectivity of inhaled 8Br-cGMP in reducing PVR compared with SVR, the thromboxane model was used to measure vascular resistance changes in response to intravenously administered 8Br-cGMP (FIG. 5). The decrease in PVR (−26%) was similar to that obtained by giving the drug via the inhaled route (−24%), but the SVR decreased much more after intravenous compared with inhaled 8Br-cGMP (−21% vs. −5%).

To determine whether the pulmonary vascular response to inhaled 8-Br-cGMP was dependent on a specific model of pulmonary hypertension, pigs were ventilated with a hypoxic gas mixture, and hemodynamic measurements were obtained as in the thromboxane model. As in the thromboxane model, PVR in this model dropped significantly more than did the corresponding SVR (28.3% vs. 8.7%, respectively p<0.01) following inhalation of 8-Br-cGMP (FIG. 6A). These results are similar even when maximal decline in PVR and SVR are compared (FIG. 6B). These data illustrate that the effects of inhaled 8-Br-cGMP are similar when two different models of pulmonary hypertension are studied.

Figure 7A:
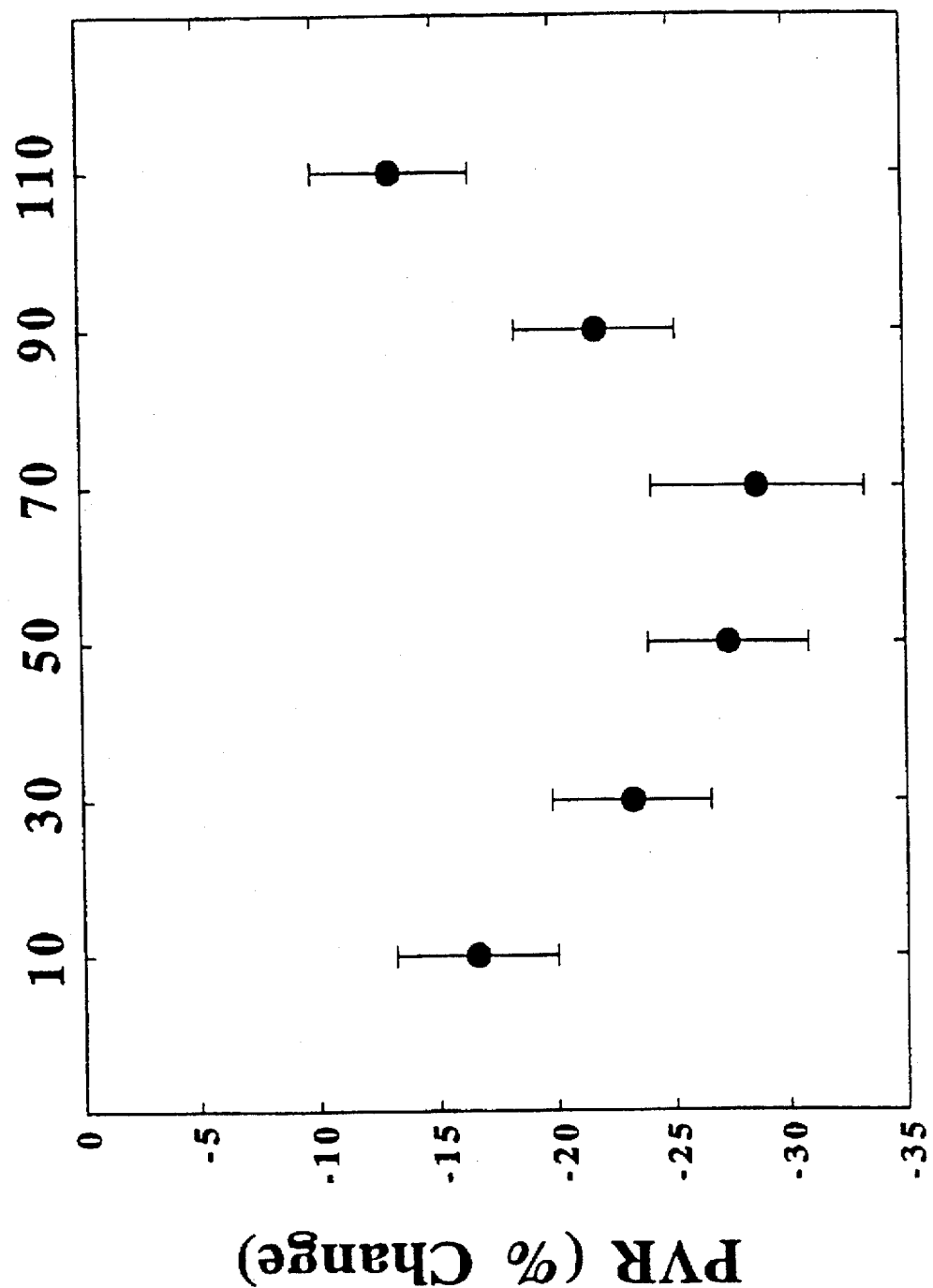

The effects of inhaled 8-Br-cGMP are time-dependent, with maximal effect occurring approximately 70 minutes after administration. These time course experiments consistently demonstrated both an initial drop in PVR as well as a gradual return to the pulmonary hypertensive baseline (FIG. 7A). 8-Br-cGMP was effective over a broad range of doses, with doses as low as 0.03 µg/kg showing a pulmonary vasodilator effect, with a maximal effect seen with doses between 2–20 µg/kg (31.5±4.5% drop in PVR, p<0.001). (FIG. 7B).

Because NO has been shown to reduce PVR in human ARDS (6), experiments were performed to investigate whether 8-Br-cGMP might act similarly in a porcine model of ARDS (n=5). Oleic acid administration caused a marked increase in PVR (FIG. 1C), a drop in arterial oxygenation (on 100% oxygen, $pO_2$ declined from 525±21 torr to 61±7 torr over the course of 5 hours), and development of edematous lungs as evidenced by copious pulmonary secretions and increased lung weights at autopsy (6.3±1.6 mg/kg control vs. 13.3±1.4 mg/kg oleic acid). In this model, 8Br-cGMP decreased PVR significantly when compared with normal saline control (−34.3±8% vs. 3.35±1.5%, p<0.05). Compared with the other models, the decrease in PVR compared with SVR only tended towards pulmonary selectivity (34±8% decline vs. 27±11% decline for PVR and SVR, respectively, p=NS).

A comparison of the pulmonary vasodilating effects between 8Br-cGMP and NO was performed in the thromboxane (n=3) and oleic acid (n=3) models. In the thromboxane model, NO reduced PVR by 46.8±7.3% while inhaled 8Br-cGMP decreased PVR by 23.9% (p=NS). In the oleic acid model, 8-Br-cGMP tended to be more effective than NO at reducing PVR (−34.3±8.0% for 8-Br-cGMP vs. −18.7±4.5% for oleic acid, p=NS).

Although cardiac outputs increased slightly following 8-Br-cGMP (FIGS. 4A–4H), data of others (11–14) suggests that stimulation of the NO pathway may result in depression of myocardial contractility, which would be of clinical concern in patients with compromised ventricular function. The effect of inhaled 8-Br-cGMP on load-independent measures of cardiac contractility was investigated using a left ventricular conductance catheter and varying preload by controlling blood return via the inferior vena cava. To establish a control for this detection method, intravenous esmolol (40 mg) was given as a bolus injection, which demonstrated a clear-cut negative inotropic effect (FIG. 8C). In contrast, inhalation of 8Br-cGMP at a dose associated with a pulmonary vasodilator effect (30 µg/kg) did not alter ventricular performance (n=2) (FIG. 8B).

Sp-8-Br-cGMPS

Sp-8-Br-cGMPS was administered in the thromboxane model as above, resulting in a drop in PVR of 62%. However, SVR also decreased by 40%. Thus, in this model, Sp-8-Br-cGMPS had a strong effect on PVR, also demonstrating relative selectivity (FIG. 9).

Permeabilizing Solvents

Figure 10:
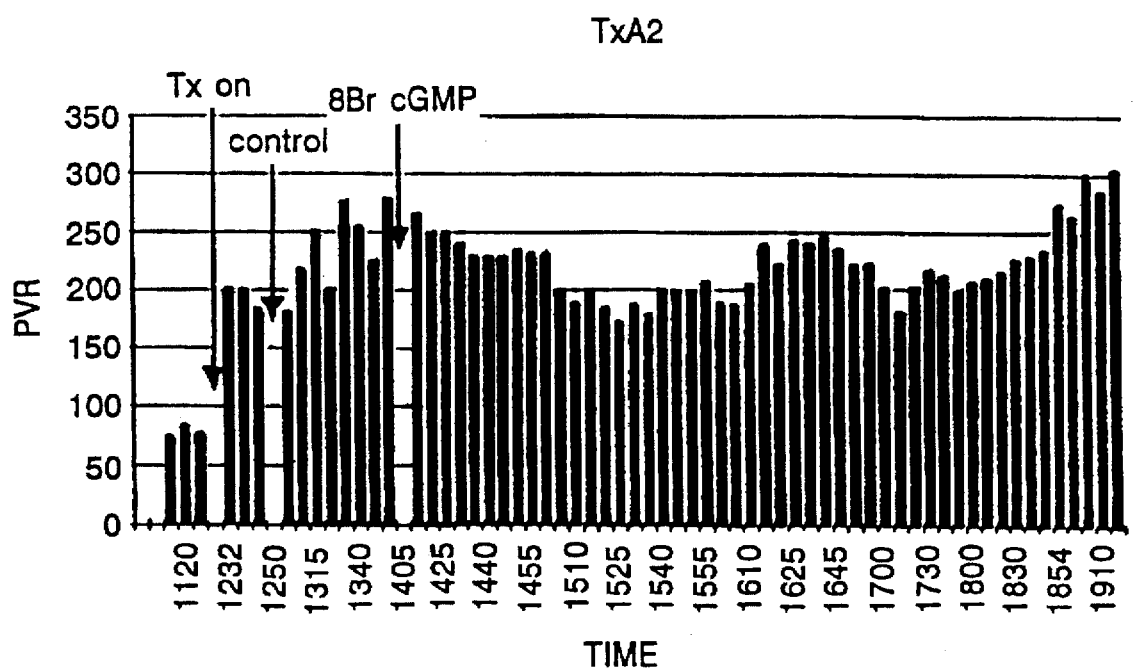
FIG. 10: Effect of inhalation of 8-Br-cGMP solubilized in DMSO.

Although the experiments consistently demonstrate that 8-Br-cGMP selectively lowers PVR, the magnitude of this effect can be enhanced by increasing the ability of 8-BrcGMP to penetrate cell membranes. This has been done by solubilizing the 8-Br-cGMP in the solvent dimethyl sulfoxide (DMSO), with similar administration as above. When 8-Br-cGMP is mixed in this way and subsequently inhaled, it causes a 37% drop in PVR in the thromboxane-induced pulmonary hypertension model (FIG. 10).

Dibutyryl cAMP

Figure 11:
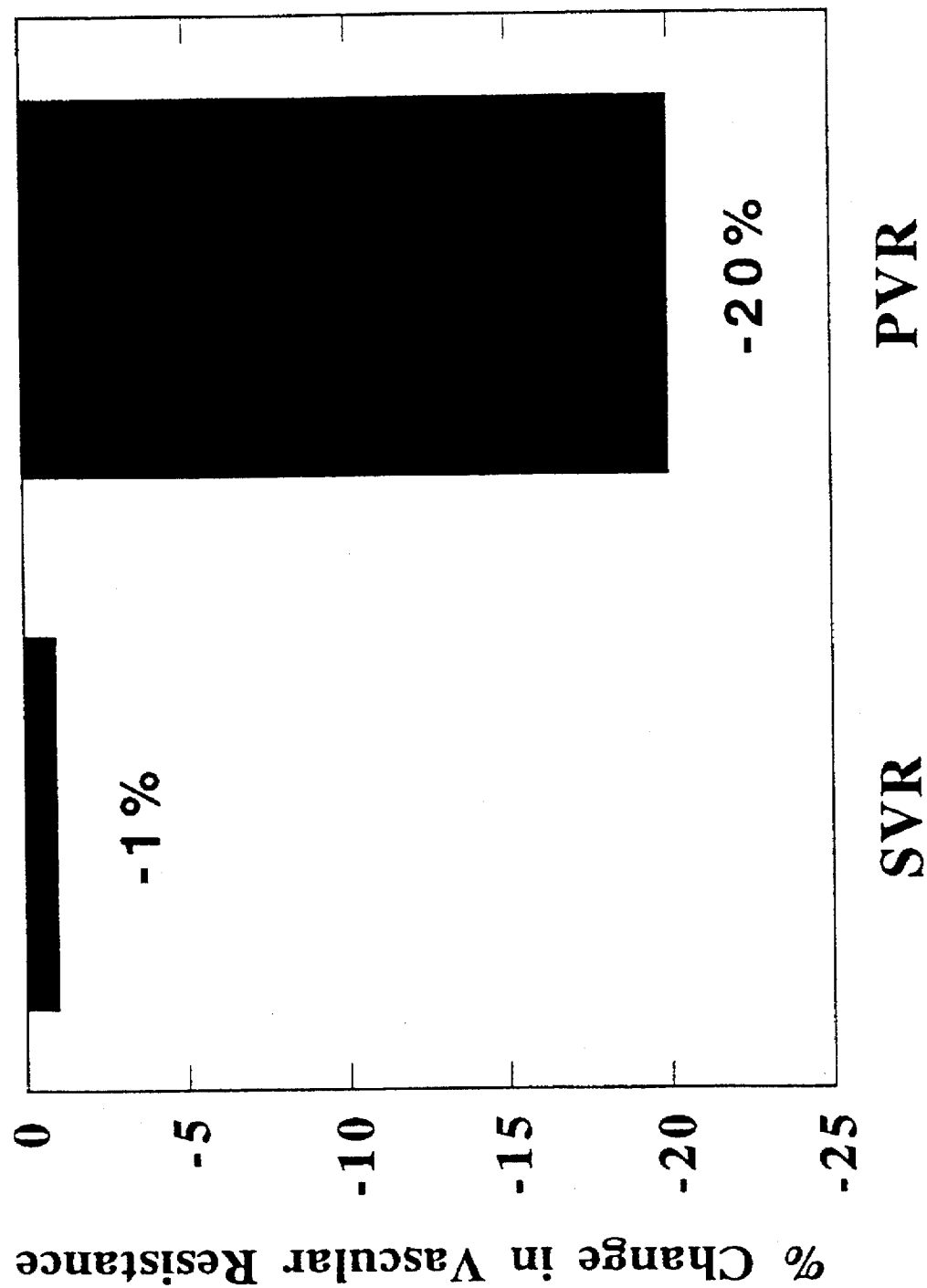
FIG. 11: Percent change in SVR and PVR upon administration of dibutyryl-cAMP solubilized in DMSO (Thromboxane model).

Dibutyryl cAMP solubilized in DMSO was administered in the thromboxane model. Dibutyryl cAMP caused a 20% drop in PVR with little effect on systemic vascular resistance (FIG. 11).

8-Br-cAMP

Figure 12:
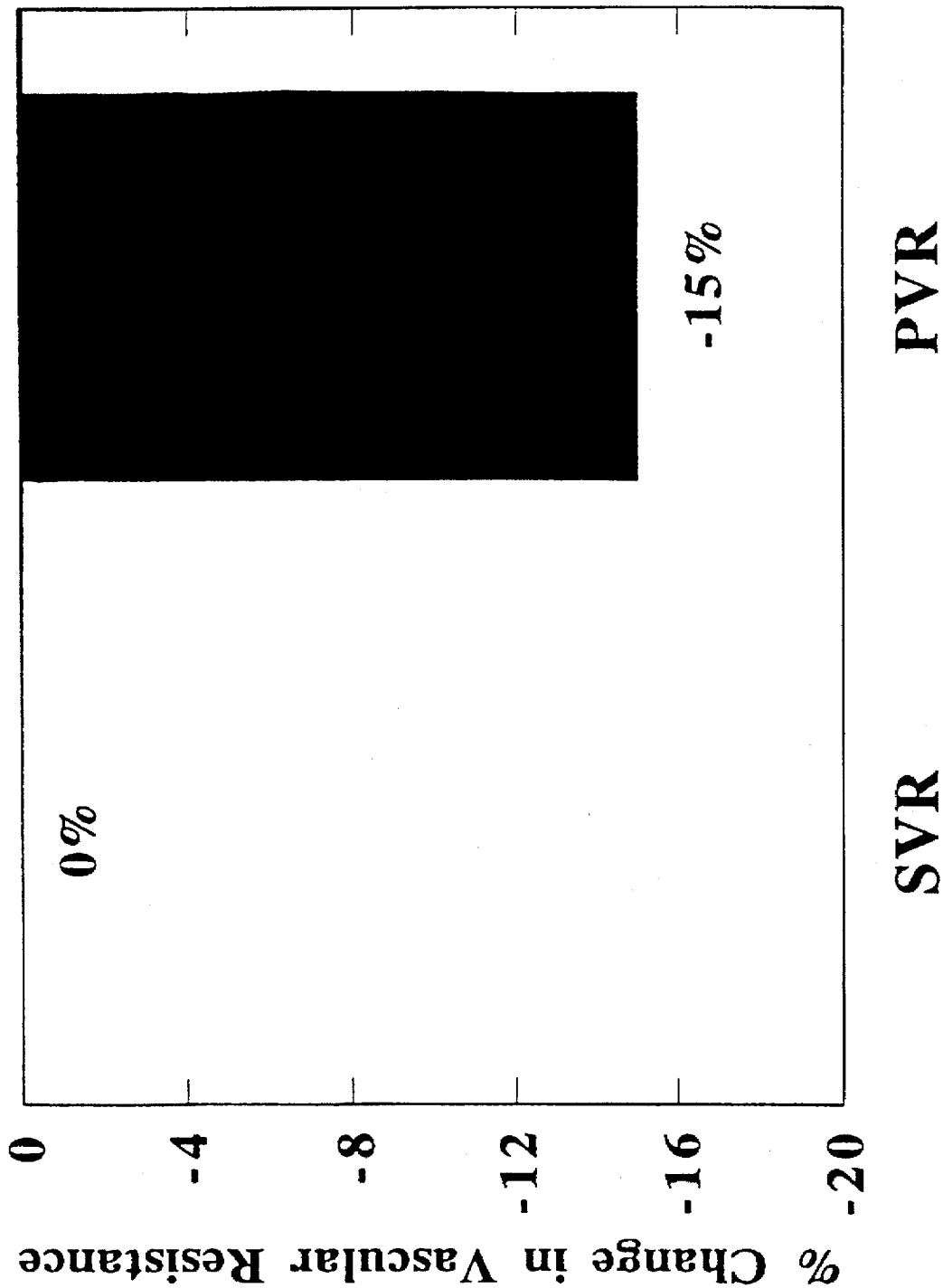
FIG. 12: Percent change in SVR and PVR upon administration of 8-Br-cAMP (Hypoxia model).

8-Br-cAMP was administered in the hypoxia model as described. Pulmonary vascular resistance was selectively reduced with no measurable effect on systemic vascular resistance (FIG. 12).

Phosphodiesterase Inhibitors

To exclude a role for activation of purinergic receptors in the lungs (17) to explain how 8-Br-cGMP might cause a decline in PVR, inhaled 8-bromoguanosine-5'-monophosphate was administered in the thromboxane analog model and found to have no effect on PVR or SVR (n=2). Because NO and 8-Br-cGMP drop PVR, this implicated a role for cGMP in pulmonary vasodilation. To explore this possibility further, the phosphodiesterase inhibitor M & B 22948 (Zaprinast), which specifically inhibits the degradation of endogenous cGMP was administered via inhalation. In this pilot study of two animals, Zaprinast decreased PVR more than SVR (41±27% decrease vs 20±11% decrease, respectively). These data suggest that elevating endogenous levels of cGMP or inhaling cGMP analogs can effectively lower pulmonary vascular resistance.

Figure 13:
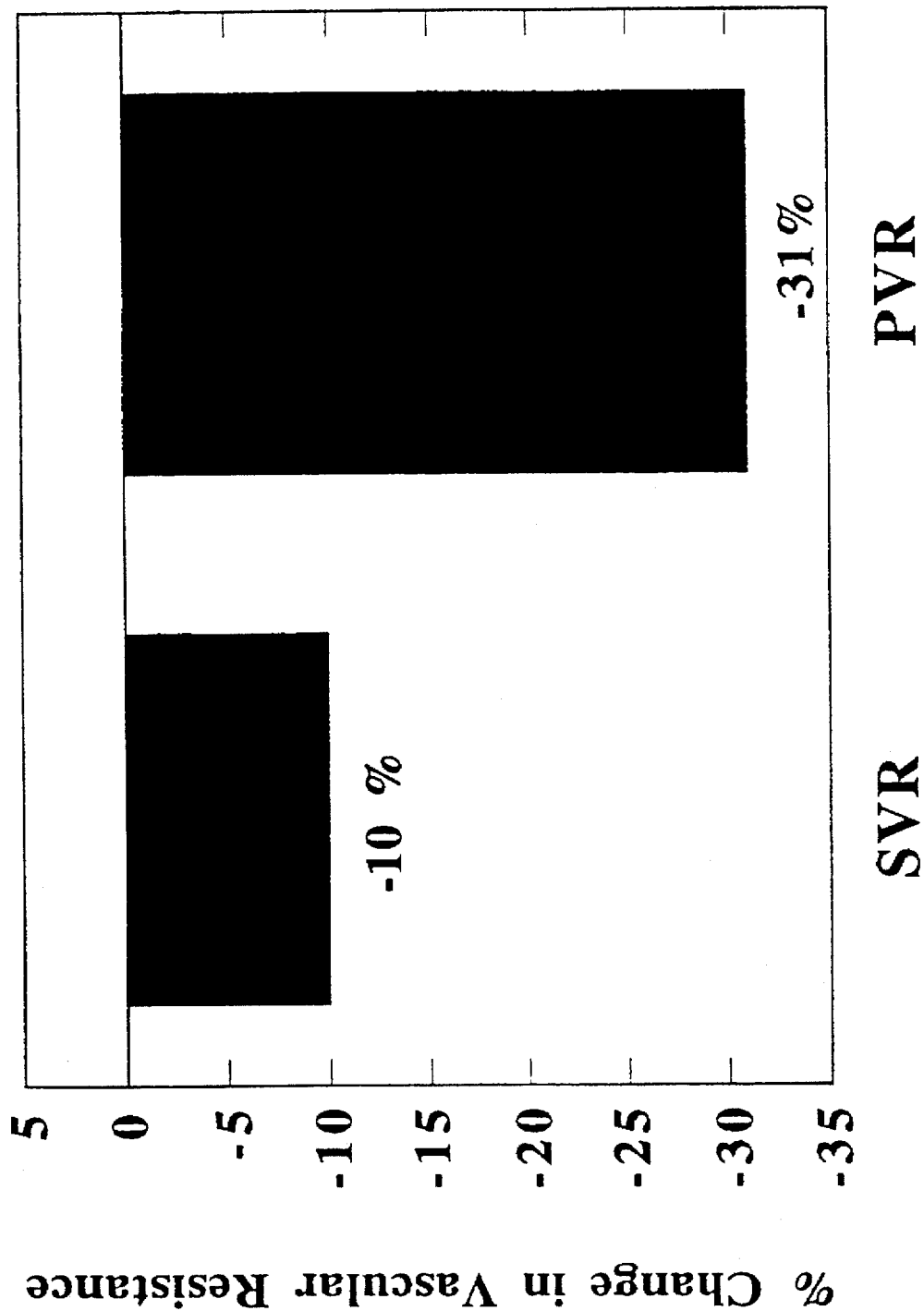
FIG. 13: Percent change in SVR and PVR upon administration of IBMX (Hypoxia model).

It was further hypothesized that inhalational administration of a compound that retards degradation of cGMP and cAMP would result in higher levels of the endogenous compounds, thereby lowering pulmonary pressures. To test this hypothesis, phosphodiesterase inhibitor (phosphodiesterases break down cAMP and cGMP, and can be selective for either compound or break down both) called isobutylmethylxanthine (IBMX) was administered. The inhalational administration of IBMX caused a drop in pulmonary vascular resistance (FIG. 13) with much less of an effect on systemic vascular resistance (in the hypoxia model). This indicates that not only can there be benefit by inhaling the cyclic nucleotides themselves, but there can be benefit by inhaling a compound which retards their degradation.

EXPERIMENTAL DISCUSSION

Both primary and secondary pulmonary hypertension are associated with extremely high morbidity and mortality. Although many therapeutic agents have been tried in order to lower the elevated pulmonary vascular resistance associated with these conditions no agent has been found effective (1,18–20). The efficacy of these agents is uniformly limited by the nonspecific nature of the vasodilation, in that systemic vascular resistance is often lowered to a similar or greater degree than pulmonary vascular resistance, occasionally causing a precipitous drop in blood pressure resulting in patient death (1,19,21). A drug is considered to be clinically effective in pulmonary hypertension if it can lower PVR more than it lowers SVR, i.e., is relatively selective for the pulmonary vasculature (1). Since most patients with chronic pulmonary hypertension die from right ventricular failure, a goal of drug therapy would be reduction of pulmonary artery pressures and calculated PVR, and normalization of cardiac output (20). In 1991, reports began to emerge concerning the use of an inhaled gas, nitric oxide, to provide selective pulmonary vasodilation in pulmonary hypertension (2,3). Rationale for the use of nitric oxide to treat pulmonary hypertension is based upon its ability to stimulate soluble guanylyl cyclase found in smooth muscle cells throughout the vasculature, leading to an increase in intracellular cGMP and subsequent vasodilation (22). Because nitric oxide binds rapidly and avidly to hemoglobin, it preferentially dilates the pulmonary vasculature. Recent clinical studies in ARDS demonstrate that this therapy is likely to benefit patients during continuous administration (6). There are practical and theoretical concerns to NO administration however: being a gas, special delivery equipment is required, and its effects are dependent on continuous administration (3,6); its free radical structure makes it highly reactive with oxygen atoms, producing toxic peroxynitrite metabolites (4,5); and its carcinogenic potential is yet to be defined, but it has been reported to produce a positive Ames test for mutagenicity (4).

To overcome these limitations, it was hypothesized that administration of a stable lipid soluble analog of cGMP (8-Br-cGMP) might have similar beneficial pulmonary vasodilating effects. In isolated lung models, this agent administered intravenously effectively reduces hypoxia-induced pulmonary vasoconstriction (23). Although others have given 8-Br-cGMP intravenously (24), this method of administration would confer no differential benefit upon the pulmonary vasculature. Because 8-Br-cGMP is in itself not specific for the pulmonary cGMP-dependent protein kinase, it was hypothesized that inhalation of aerosolized 8-Br-cGMP would produce the highest possible pulmonary concentrations, thereby conferring selective reduction of pulmonary vascular resistance.

Three models of pulmonary hypertension were established. Because thromboxane is thought to play a role in pulmonary hypertension in diseases as varied as scleroderma, systemic lupus erythematosus, cirrhosis of the liver, and pulmonary emboli (25–33), the thromboxane analog U-46619,9,11-dideoxy-11α, 9α-epoxymethanoprostaglandin $F_{2\alpha}$ (10) was infused to induce pulmonary hypertension. This model was well suited to measuring the effects of pharmacologic intervention, because after a 60–90 minute period of stabilization during which constant doses of this analog were infused, hemodynamic measurements remained stable (see FIGS. 2A–E). In addition, others have shown that endothelium-derived relaxing factor (nitric oxide or related compounds) plays a significant role in blunting the pulmonary response to vasoconstrictors such as thromboxane (10), making this model ideal to test the effects of a cGMP analog. These studies demonstrate that inhalation of aerosolized 8-Br-cGMP causes a significant decline in pulmonary vascular resistance, with minimal effects on systemic vascular resistance and left ventricular contractile strength. After a single dose of 8-Br-cGMP, the drop in PVR was over 50% of that achieved with continuous nitric oxide inhalation under identical conditions. In contrast with NO, however, the effects of 8-Br-cGMP were longer-lived, lasting up to 2 hours (nitric oxide's effects were completely gone within 4 minutes of discontinuation).

Because many clinical conditions are associated with hypoxemia, the effects of ventilation with a hypoxic gas mixture were investigated. Hypoxia-induced vasoconstriction has been well described (34,35), and is frequently used as a model system to study pulmonary hypertension (3,36). The levels of hypoxia used in the present study (inhaled 9–10%) were chosen as the minimal levels tolerated by the animals without the development of metabolic acidosis (lowest average pH 7.36±0.02) or circulatory collapse. Because small variations in inspired $O_2$ caused large fluctuations in PVR, inhaled $O_2$ was continuously monitored with frequent sampling of arterial $pO_2$ ($pO_2$ 36.5±2.2 mmHg at lowest PVR value). As in the thromboxane model, aerosolized 8-Br-cGMP caused a selective reduction in PVR. For both the thromboxane-induced and hypoxia-induced pulmonary hypertension models, the effects of inhaled 8-Br-cGMP were time- and dose-dependent, with maximal effects seen at about 70 minutes following administration, at doses between 2–20 µg/kg. This data suggests that clinical conditions with elevated pulmonary vascular resistances associated with hypoxemia (such as congenital heart disease, sleep apnea syndrome, or end-stage pulmonary disease (37)) may potentially benefit from inhalation of compounds augmenting cGMP levels.

As a third model to test the effects of inhaled 8-Br-cGMP, an ARDS-like condition was created by intravenous injection of oleic acid (38–42), which manifested as elevated PVR, pulmonary exudation, and hypoxemia, characteristic of human ARDS. These characteristics are similar to those described by others using this same model (38–42). Because the permeability of the lungs is markedly increased following oleic acid administration (41), corroborated by increased lung weights in the oleic acid-treated pigs compared to controls in our experiments, it is possible that inhalation of 8-Br-cGMP results in greater systemic delivery in this model compared with the thromboxane- and hypoxia-induced pulmonary hypertension models. This may explain why SVR declined more in the ARDS model following 8-Br-cGMP administration than in the other models. This is consistent with the observation that intravenous infusion of 8-Br-cGMP causes systemic vasodilation (24), explaining why the trend of 8-Br-cGMP as a selective pulmonary vasodilator in this model did not achieve statistical significance. Although NO has been shown to improve oxygenation in human ARDS (6), its effect in this model was minimal ($pO_2$ changed from 74 to 76 mm Hg after 10 minutes of continuous administration of NO 50 ppm); the effects of inhaled 8-Br-cGMP on systemic oxygenation in our study were similarly unimpressive. This may have been due to the fulminant nature of the oleic acid-induced ARDS, and the rapid deterioration of the pig over the course of each experiment. In a control experiment in which oleic acid was given and effects on oxygenation were observed without 8-Br-cGMP, oxygenation rapidly deteriorated. This decline in arterial oxygenation over time may obscure a small increase caused by an experimental therapy which takes over an hour to achieve peak effect.

There is a theoretical concern that stimulation of the nitric oxide pathway might depress myocardial contractility, which would be of clinical concern in patients with cor pulmonale. Depression of myocardial contractility has been ascribed to nitric oxide production (11–13), and 8-Br-cGMP itself has been shown to exert a moderate negative inotropic effect on isolated ferret cardiac muscle (14), so it was important to measure the effect of inhaled 8-Br-cGMP on load-independent measures of myocardial contractility. Because load-independent measures of right ventricular performance are difficult to obtain and remain to be validated (43), this data uses pressure-volume loops to construct load-independent measures of left ventricular function following inhalation of 8-Br-cGMP. In this study, inhalation of 8-Br-cGMP at an effective pulmonary vasodilating dose has no effect on left ventricular ESPVR suggesting no effect on contractile strength.

To understand the mechanism whereby 8-Br-cGMP acts as a pulmonary vasodilator, 8-Br-guanosine 5'monophosphate was administered to exclude a role for purinergic receptor activation at pharmacologic doses. These receptors are widely distributed in the pulmonary vasculature and are known to affect smooth muscle tone (17). This compound had no effect in decreasing PVR when given at a dose at which 8-Br-cGMP demonstrates a clear-cut decline in PVR (270 µg/kg). This suggests that 8-Br-cGMP's ability to reduce PVR is related to its actions as a second messenger cyclic nucleotide.

In conclusion, inhalation of 8-Br-cGMP provides selective pulmonary vasodilation in two clinically relevant models of pulmonary hypertension. These effects are likely to be mediated by its effects as a second messenger cyclic nucleotide. The combination of an agent which stimulates the NO/cGMP pathway with a directed method of delivery (such as inhalation) suggests a broad range of pharmacologic possibilities for the treatment of diseases resulting in pulmonary hypertension.

REFERENCES

1. Packer, M. Vasodilator therapy for primary pulmonary hypertension. Ann. of Int. Med. 1985. 103(2) 258–270.
2. Pepke-Zaba J. Higenbottam T. W., Dinh-Xuan A. T., Stone D., and Wallwork J. Inhaled nitric oxide as a cause of selective pulmonary vasodilation in pulmonary hypertension. Lancet. 1991. 338(8776) 1173–1174.
3. Frostell C., Fratacci M., Wain J., Jones R., and Zapol W. Inhaled nitric oxide: a selective pulmonary vasodilator reversing hypoxic pulmonary vasoconstriction. Circ. 1991. 83(6) 2038–2047.
4. Arroyo P. L., Hatch-Pigott V., Mower H. F., Cooney R. V. Mutagenicity of nitric oxide and its inhibition by antioxidants. Mutation Research. 1992; 281: 193–202.
5. Beckman J. S., Beckman T. W., Chen J., Marshall P. A., Freeman B. A. Apparent hydroxyl radical production by peroxynitrite: Implications for endothelial injury from nitric oxide and superoxide. Proc. Natl. Acad. Sci. USA. 1990; 87: 1620–1624.
6. Rossaint R., Falke K., Lopez F., Slama K., Pison U., Zapol W. Inhaled nitric oxide for the adult respiratory distress syndrome. N. Engl. J. Med. 1993. 328(6) 399–405.
7. Lincoln T. M., and Cornwell T. L. Intracellular cyclic GMP receptor proteins. FASEB J. 1993; 7: 328–338.
8. Murad F. Cyclic guanosine monophosphate as a mediator of vasodilation. J. Clin. Invest. 1986; 78: 1–5.
9. Kuo J. F. Molecular and physiopathologic aspects of mammalian cyclic GMP-dependent protein kinase. Ann. Rev. Pharmacol. Toxicol. 1978; 18: 341–355.
10. Fineman J., Chang R., Soifer S. EDRF inhibition augments pulmonary hypertension in intact newborn lambs. Am. J. Physio. 1992 262(3) H1365–1371.
11. Balligand J.-L., Ungureanu D., Kelly R. A., Kobzik L., Pimental D., Michel T., Smith T. W. Abnormal contractile function due to induction of nitric oxide synthesis in rat cardiac myocytes follows exposure to activated macrophage-conditioned medium. J. Clin. Invest. 1993; 9: 2314–2319.
12. Brady A. J. B., Poole-Wilson P. A., Harding S. E., Warren J. B. Nitric oxide within cardiac myocytes reduces their contractility in endotoxemia. Am. J. Physiol. 1992; 263: H1963–H1966.
13. Finkel M. S., Oddis C. V., Jacob T. D., Watkins S. C., Hattler B. G., Simmons R. L. Negative inotropic effects of cytokines on the heart mediated by nitric oxide. Science. 1992; 257(5068): 387–389.
14. Shah A. M., Lewis M. J., Henderson A. H. Effects of 8-Bromo-cyclic GMP on contraction and on inotropic response of ferret cardiac muscle. J. Mol. Cell Cardiol. 1991; 23: 55–64.
15. Baan J., van der Velde E. T., DeBruin H. G., Smeenk G. J., Koops J., Van Dijk A. D., Temmerman D., Senden J. Buis B. Continuous measurement of left ventricular volume in animals and humans by conductance catheter Circ. 1984; 70: 812–823.
16. Sagawa K. The ventricular pressure-volume diagram revisited. Circ. Res. 1978; 43: 677–687.
17. Dubyak G. R. Signal transduction by $P_2$-purinergic receptors for extracellular ATP. Am. J. Respir. Cell Mol. Biol. 1991; 4: 295–300.
18. Priebe, H.-J. Efficacy of vasodilator therapy in a canine model of acute pulmonary hypertension Am. J. Physiol. 1988. 255(5, pt.2). H1232–1239.
19. Weir E. K., Rubin L. J., Ayers S. M., Bergofsky E. H., Brundage B. H., Detre K. M., Elliott C. G., Fishman A. P., Goldring R. M., Groves B. M., Kernis J. T., Koerner S. K., Levy P. S., Pietra G. G., Reid L. M., Rich S., Vriem C. E., Williams G. W., and Wu M. The acute administration of vasodilators in primary pulmonary hypertension. Experience from the National Institutes of Health registry on primary pulmonary hypertension. Am. Rev. Respir. Dis. 1989. 140(6) 1623–1630.
20. Rich. S. Should patients with pulmonary hypertension and increased pulmonary resistance be treated with vasodilators? Cardiovasc. Clin. 1990. 21(1) 265–274.
21. Partanen J. Nieminen M., Luomanmaki K. Death in a patient with primary pulmonary hypertension after 20 mg of Nifedipine (letter). NEJM. 1993; 329(11: 812–813.
22. Ignarro L. Biosynthesis and metabolism of endothelium-derived nitric oxide. Annu. Rev. Pharmacol. Toxicol. 30:535–560, 1990.
23. Archer S., Rist K., Nelson D., DeMaster E., Cowan N., Weir E. Comparison of the hemodymanic effects of nitric oxide and endothelium-dependent vasodilators in intact lungs. 1990. J. Appl. Physiol. 68(2) 735–747.
24. Elsner D., Kromer E., and G. Riegger. Hemodynamic, renal, and hormonal effects of 8-Br-cyclic GMP in conscious dogs with and without congestive heart failure. Journal of Cardiovascular Pharmacology. 1989. 14. 241–247.
25. Zamora C. A., Baron D. A., and Heffner J. E. Thromboxane contributes to pulmonary hypertension in ischemia-reperfusion lung injury. J. Appl. Physiol. 1993 74(1) 224–229.
26. Christman B. W., McPhereson C. D., Newman J. H., King G. A., Bernard G. R., Groves B. M., and Loyd J. E. An imbalance between the excretion of thromboxane and prostacyclin metabolites in pulmonary hypertension. N. Engl. J. Med. 1992. 327(2) 70–75.
27. Ostenden J., Hede R., Myreng Y., Ege T., and E. Holtz. Intravenous injection of Albunex microspheres causes thromboxane-mediated pulmonary hypertension in pigs, but not in monkeys or rabbits. Acta Physiol. Scand. 1992. 144(3) 307–315.
28. Byrick, R. J., Mullen J. B., Wong P. Y., Kay J. C., Wigglesworth D., and R. J. Doran. Prostanoid production and pulmonary hypertension after fat embolism are not modified by methylprednisolone. Ca. J. Anaesth. 1991. 385(5) 660–667.
29. Nuttal G. A., Murray M. J., and E. J. W. Bowie. Protamine-heparin-induced pulmonary hypertension in pigs: effects of treatment with a thromboxane receptor antagonist on hemodynamics and coagulation. Anesthesiology. 1991. 74 (1) 138–145.
30. Badesch D. B., Orton E. C., Zapp L. M., Westcott J. Y., Hester J., Voelkel N. F., and K. R. Stenmark. Decreased arterial wall prostaglandin production in neonatal calves with severe chronic pulmonary hypertension. Am. J. Respir. Cell. Mol. Biol. 1989.1 (6) 489–498.
31. Rostagno C., Gensini G. F., Boncinelli S., Marsili M., Castellani S., Lorenzi P., Merciai V., Linden M., Chelucci G. L., F. Cresci. The prominent role of thromboxane A2 formation on early pulmonary hypertension induced by oleic acid administration in sheep. Thromb. Res. 1990. 58(1) 35–45.
32. Pinheiro, J. M., Pitt B. R., and C. N. Gillis. Roles of platelet-activating factor and thromboxane in group B streptococcus-induced pulmonary hypertension in piglets. Pediatr. Res. 1989. 26(5) 420–424.
33. Seeger W., Walter H., Suttorp N., Muhly M., and S. Bhakdi. Thromboxane-mediated hypertension and vascular leakage evoked by low doses of *E. coli* hemolysin in rabbit lungs. J. Clin. Invest. 1989. 84(1) 220–227.
34. Morgan J. M., Griffiths M., Du Bois R. M., Evans T. W. Hypoxic pulmonary vasoconstriction in systemic sclerosis and primary pulmonary hypertension. Chest. 1991; 99(3): 551–556. 35. Agusti A. G. N., Barbara J. A., Roca J., Wagner P. D., Guitart R., Rodriguez-Roison R. Hypoxic pulmonary vasoconstriction and gas exchange in exercise in chronic obstructive pulmonary disease. Chest. 1990; 97(2): 268–275.
36. Frostell C. G., Blomqvist H., Hedenstierna G., Lundberg J., Zapol W. M. Inhaled nitric oxide selectively reverses hypoxic pulmonary vasoconstriction without causing systemic vasodilation. Anesthesiology. 1993; 78(3): 427–434.
37. Textbook of internal medicine.
38. Halden E., Hedstrand U., and K. Torsner. Oleic acid lung damage in pigs. Acta Anaesth. Scand. 1982. 26. 121–125.
39. Peltier L. Fat embolism III: the toxic properties of neutral fat and free fatty acids. Surgery. 1956. 40. 665.
40. Ashbaugh D., Uzawa T. Respiratory and hemodynamic changes after injection of free fatty acids. J. Surg. Res. 1968. 8. 417.
41. Hofman W., Ehrhart I., Granger W., and D. Miller. Sequential cardiopulmonary changes after oleic-acid injury in dogs. Critical Care Med. 1985 13(1). 22–27.
42. Cabrera M., Nakamura G., Montague D., and R. Cole. Effect of airway pressure on pericardial pressure. Am. Rev. Respir. Dis. 1989. 140. 659–667.
43. Burkhoff, Right heart conductance measurement

What is claimed is:

1. A method for treating pulmonary hypertension in a subject comprising selectively decreasing pulmonary vascular resistance in the subject which comprises administering endotracheally or endobronchially an effective amount of a drug selected from the group consisting of cyclic nucleotides and phosphodiesterase inhibitors or administering an effective amount of a phosphodiesterase inhibitor by injecting a liquid containing the phosphodiesterase inhibitor via the trachea or a bronchus.

2. The method of claim 1 wherein the ratio of the percent change in systemic vascular resistance to the percent change in the pulmonary vascular resistance is about 0.5 or less.

3. The method of claim 1, wherein the ratio of the percent change in systemic vascular resistance to the percent change in the pulmonary vascular resistance is about 0.3 or less.

4. The method of claim 1 wherein the ratio of the percent change in systemic vascular resistance to the percent change in the pulmonary vascular resistance is about 0.04 or less.

5. The method of claim 1, wherein the subject is a mammal.

6. The method of claim 5 wherein the mammal is a pig.

7. The method of claim 5 wherein the mammal is a human.

8. The method of claim 1, wherein the administering comprises injecting a liquid containing the drug via the trachea or a bronchus.

9. The method of claim 1, wherein the administering comprises inhaling the drug in an aerosol form.

10. The method of claim 9 wherein the aerosol is generated by a nebulizer.

11. The method of claim 9 wherein the aerosolized drug is administered as an aqueous solution.

12. The method of claim 9 wherein the areosolized drug is administered as an micronized power.

13. The method of claim 1, wherein the pulmonary vascular resistance is decreased by at least about twenty-four percent.

14. The method of claim 1, wherein the pulmonary vascular resistance is decreased by up to about sixty-four percent.

15. The method of claim 1, wherein the pulmonary vascular resistance is decreased between about twenty-four percent and about sixty-four percent.

16. The method of claim 1, wherein the pulmonary vascular resistance is decreased for over ninety minutes.

17. The method of claim 1, wherein the phosphodiesterase inhibitors are selected from the group consisting of isobutylmethylxanthine, 1,3-dihydro-3,3-dimethyl-5-(1,4,5,6-tetrahydro-6-oxo-3-pyridazinyl)-2H-indol-2-one, 4-[3-(cyclopentyloxy)-4-methoxyphenyl]-2-pyrrolidinone, 2-o-propoxyphenyl-8-azapurin-6-one, 2,3,6,7-tetrahydro-9,10-dimethoxy-3-methyl-2-[(2,4,6-trimethylphenyl)imino]-4H-pyrimido[[6,1,-$\alpha$]isoquinolin-4-one, 5-amino-(3,4'-bipyridin)-6(1H)-one, and 1,6-dihydro-2-methyl-6-oxo-(3,4'bipyridine)-5-carbonitrile.

* * * * *

UNITED STATES PATENT AND TRADEMARK OFFICE
CERTIFICATE OF CORRECTION

PATENT NO. : 5,728,705
DATED : March 17, 1998
INVENTOR(S) : Charles A. Lawson, David J. Pinsky, Arthur Smerling, and David M. Stern It is certified that error appears in the above-identified patent and that said Letter Patent is hereby corrected as shown below:

column 3, line 45: "DETAILED OF" should read --DETAILED DESCRIPTION OF--
column 5, line 42: "5' cyclic" should read --5'-cyclic--
column 6, line 7: "rolipram, 4-[3 (cyclopentyloxy)" should read
            --rolipram, 4-[3-(cyclopentyloxy)--
    line 13: "(1H) one and" should read --(1H)-one, and--
column 7, line 5: "and 9±4%, respectively was" should read --and 9±4%, respectively) was--
column 8, line 62: "PVR=80-" should read --PVR=80·--
    line 63: "SVR=80.(MAP" should read --SVR=80·(MAP--
column 17, line 13: "micronized power" should read --micronized powder--
column 18, line 1: "claim 1" should read --claim 14--

Signed and Sealed this

Thirteenth Day of April, 1999

Attest:

Q. TODD DICKINSON

*Attesting Officer*    *Acting Commissioner of Patents and Trademarks*